(12) United States Patent
Hahnen et al.

(10) Patent No.: US 6,755,338 B2
(45) Date of Patent: Jun. 29, 2004

(54) MEDICAL INSTRUMENT

(75) Inventors: Kevin F. Hahnen, Duluth, GA (US); Richard A. Hillstead, Duluth, GA (US); Bryan D. Knodel, Flagstaff, AZ (US)

(73) Assignee: Cerebral Vascular Applications, Inc., Duluth, GA (US)

( * ) Notice: Subject to any disclaimer, the term of this patent is extended or adjusted under 35 U.S.C. 154(b) by 0 days.

(21) Appl. No.: 10/159,221

(22) Filed: May 31, 2002

(65) Prior Publication Data

US 2003/0045900 A1 Mar. 6, 2003

Related U.S. Application Data

(63) Continuation-in-part of application No. 09/942,236, filed on Aug. 29, 2001.

(51) Int. Cl.[7] .............................................. A61B 17/115
(52) U.S. Cl. ..................... 227/175.1; 227/19
(58) Field of Search ........................... 227/175.1–182.1, 227/19

(56) References Cited

U.S. PATENT DOCUMENTS

| | | |
|---|---|---|
| 3,643,851 A | 2/1972 | Green et al. |
| 4,202,479 A | 5/1980 | Razgulov et al. |
| 4,204,623 A | 5/1980 | Green |
| 4,207,873 A | 6/1980 | Kruy |
| 4,290,542 A | 9/1981 | Fedotov et al. |
| 4,349,028 A | 9/1982 | Green |
| 4,473,077 A | 9/1984 | Noiles et al. |
| 4,485,817 A | 12/1984 | Swiggett |
| 4,488,523 A | 12/1984 | Shichman |
| 4,566,620 A | 1/1986 | Green et al. |
| 4,576,167 A | 3/1986 | Noiles |
| 4,610,383 A | 9/1986 | Rothfuss et al. |
| 4,629,107 A | 12/1986 | Fedotov et al. |
| 4,646,745 A | 3/1987 | Noiles |
| 4,671,403 A | 6/1987 | Schick |
| 4,688,555 A | 8/1987 | Wardle |
| 4,700,703 A | 10/1987 | Resnick et al. |
| 4,728,020 A | 3/1988 | Green et al. |
| 4,821,939 A | 4/1989 | Green |
| 4,869,414 A | 9/1989 | Green et al. |
| 4,880,015 A | 11/1989 | Nierman |
| 4,919,112 A | 4/1990 | Siegmund |
| 4,944,443 A | 7/1990 | Oddsen et al. |
| 4,951,861 A | 8/1990 | Schulze et al. |
| 4,962,877 A * | 10/1990 | Hervas ..................... 227/179.1 |
| 5,018,657 A | 5/1991 | Pedlick et al. |
| 5,042,707 A | 8/1991 | Taheri |
| 5,067,964 A | 11/1991 | Richmond et al. |
| 5,174,487 A | 12/1992 | Rothfuss et al. |
| 5,199,627 A | 4/1993 | Christensen |
| 5,217,472 A | 6/1993 | Green et al. |
| 5,222,961 A | 6/1993 | Nakao et al. |
| 5,246,156 A | 9/1993 | Rothfuss et al. |
| 5,257,713 A | 11/1993 | Green et al. |
| 5,258,008 A | 11/1993 | Wilk |

(List continued on next page.)

*Primary Examiner*—Michael J. Milano
*Assistant Examiner*—D. Jacob Davis
(74) *Attorney, Agent, or Firm*—Cook,Alex,McFarron,Manzo,Cummings & Mehler, Ltd.

(57) ABSTRACT

A hydraulically actuated medical instrument includes an elongated shaft having proximal and distal ends, a hydraulically actuated end effector at the distal end of the shaft and a fluid flow path extending through the shaft to the end effector. The shaft may be capable of an angled configuration where at least a portion of the shaft is manually movable to a direction in which it extends at an angle to another portion of the shaft. The end effector is not limited to a linear configuration and at least a portion of an elongated end effector extends at an angle relative to another portion of the end effector as is needed or desirable for the particular procedure to be performed.

14 Claims, 30 Drawing Sheets

U.S. PATENT DOCUMENTS

| | | | |
|---|---|---|---|
| 5,271,543 A | 12/1993 | Grant et al. | |
| 5,289,963 A | 3/1994 | McGarry et al. | |
| 5,306,234 A | 4/1994 | Johnson | |
| 5,312,023 A | 5/1994 | Green et al. | |
| 5,312,024 A | 5/1994 | Grant et al. | |
| 5,320,269 A | 6/1994 | Deschenes et al. | |
| 5,326,013 A | 7/1994 | Green et al. | |
| 5,344,059 A | 9/1994 | Green et al. | |
| 5,348,259 A | 9/1994 | Blanco et al. | |
| 5,350,355 A | 9/1994 | Sklar | |
| 5,356,064 A | 10/1994 | Green et al. | |
| 5,364,002 A | 11/1994 | Green et al. | |
| 5,366,479 A | 11/1994 | McGarry et al. | |
| 5,376,095 A | 12/1994 | Ortiz | |
| 5,381,943 A | 1/1995 | Allen et al. | |
| 5,383,880 A | 1/1995 | Hooven | |
| 5,392,978 A | 2/1995 | Velez et al. | |
| 5,403,312 A | 4/1995 | Yates et al. | |
| 5,405,073 A * | 4/1995 | Porter | 227/175.1 |
| 5,405,344 A | 4/1995 | Williamson et al. | |
| 5,409,498 A | 4/1995 | Braddock et al. | |
| 5,423,471 A | 6/1995 | Mastri et al. | |
| 5,431,323 A | 7/1995 | Smith et al. | |
| 5,439,156 A | 8/1995 | Grant et al. | |
| 5,452,836 A * | 9/1995 | Huitema et al. | 227/176.1 |
| 5,456,401 A | 10/1995 | Green et al. | |
| 5,465,894 A | 11/1995 | Clark et al. | |
| 5,470,010 A | 11/1995 | Rothfuss et al. | |
| 5,478,003 A | 12/1995 | Green et al. | |
| 5,482,197 A | 1/1996 | Green et al. | |
| 5,484,095 A | 1/1996 | Green et al. | |
| 5,485,952 A | 1/1996 | Fontayne | |
| 5,497,933 A | 3/1996 | DeFonzo et al. | |
| 5,549,637 A | 8/1996 | Crainich | |
| 5,560,532 A | 10/1996 | DeFonzo et al. | |
| 5,562,682 A | 10/1996 | Oberlin et al. | |
| 5,573,543 A | 11/1996 | Akopov et al. | |
| 5,575,799 A | 11/1996 | Bolanos et al. | |
| 5,603,443 A | 2/1997 | Clark et al. | |
| 5,605,273 A | 2/1997 | Hamblin et al. | |
| 5,607,094 A | 3/1997 | Clark et al. | |
| 5,607,095 A | 3/1997 | Smith et al. | |
| 5,626,587 A | 5/1997 | Bishop et al. | |
| 5,626,607 A * | 5/1997 | Malecki et al. | 606/205 |
| 5,632,432 A | 5/1997 | Schulze et al. | |
| 5,634,584 A | 6/1997 | Okorocha et al. | |
| 5,636,780 A | 6/1997 | Green et al. | |
| 5,643,319 A | 7/1997 | Green et al. | |
| 5,645,209 A | 7/1997 | Green et al. | |
| 5,647,526 A | 7/1997 | Green et al. | |
| 5,662,662 A | 9/1997 | Bishop et al. | |
| 5,680,982 A | 10/1997 | Schulze et al. | |
| 5,690,269 A | 11/1997 | Bolanos et al. | |
| 5,702,408 A | 12/1997 | Wales et al. | |
| 5,704,534 A | 1/1998 | Huitema et al. | |
| 5,713,505 A | 2/1998 | Huitema | |
| 5,725,536 A | 3/1998 | Oberlin et al. | |
| 5,725,556 A | 3/1998 | Moser et al. | |
| 5,732,871 A | 3/1998 | Clark et al. | |
| 5,743,456 A | 4/1998 | Jones et al. | |
| 5,749,893 A | 5/1998 | Vidal et al. | |
| 5,766,169 A | 6/1998 | Fritzsch et al. | |
| 5,782,397 A | 7/1998 | Koukline | |
| 5,794,834 A | 8/1998 | Hamblin et al. | |
| 5,797,536 A | 8/1998 | Smith et al. | |
| 5,797,537 A | 8/1998 | Oberlin et al. | |
| 5,797,538 A | 8/1998 | Heaton et al. | |
| 5,817,109 A | 10/1998 | McGarry et al. | |
| 5,820,009 A | 10/1998 | Melling et al. | |
| 5,823,066 A | 10/1998 | Huitema et al. | |
| 5,829,662 A | 11/1998 | Allen et al. | |
| 5,833,695 A | 11/1998 | Yoon | |
| 5,851,214 A | 12/1998 | Larsen et al. | |
| 5,855,311 A | 1/1999 | Hamblin et al. | |
| 5,865,361 A | 2/1999 | Milliman et al. | |
| 5,901,895 A | 5/1999 | Heaton et al. | |
| 5,947,362 A | 9/1999 | Omli | |
| 5,954,746 A | 9/1999 | Holthaus et al. | |
| 6,074,401 A | 6/2000 | Gardiner et al. | |
| 6,119,913 A | 9/2000 | Adams et al. | |
| 6,149,658 A | 11/2000 | Gardiner et al. | |
| 6,190,401 B1 | 2/2001 | Green et al. | |
| 6,241,139 B1 | 6/2001 | Milliman et al. | |
| 6,241,140 B1 | 6/2001 | Adams et al. | |
| 6,250,532 B1 | 6/2001 | Green et al. | |
| 6,264,086 B1 | 7/2001 | McGuckin, Jr. | |
| 6,270,516 B1 | 8/2001 | Tanner et al. | |
| 6,273,903 B1 | 8/2001 | Wilk | |
| 6,302,311 B1 | 10/2001 | Adams et al. | |
| 6,312,437 B1 | 11/2001 | Kortenbach | |
| 6,315,715 B1 * | 11/2001 | Taylor et al. | 600/140 |
| 6,330,965 B1 | 12/2001 | Milliman et al. | |
| 6,368,341 B1 | 4/2002 | Abrahamson | |
| 2001/0018553 A1 | 8/2001 | Krattiger et al. | |
| 2001/0030219 A1 | 10/2001 | Green et al. | |
| 2001/0041893 A1 | 11/2001 | Bartel | |
| 2001/0053874 A1 | 12/2001 | Pauker | |
| 2002/0004663 A1 | 1/2002 | Gittings et al. | |

\* cited by examiner

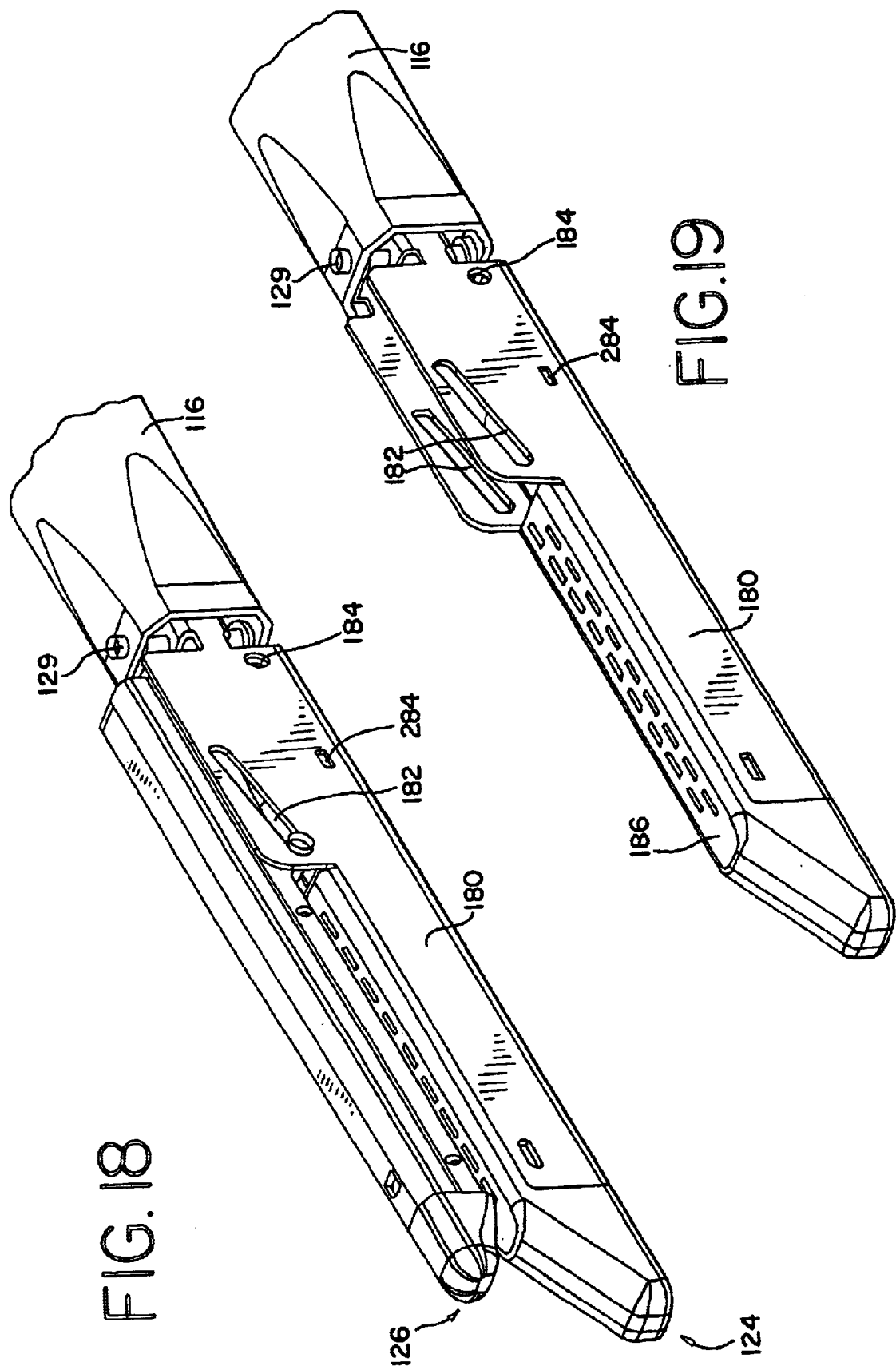

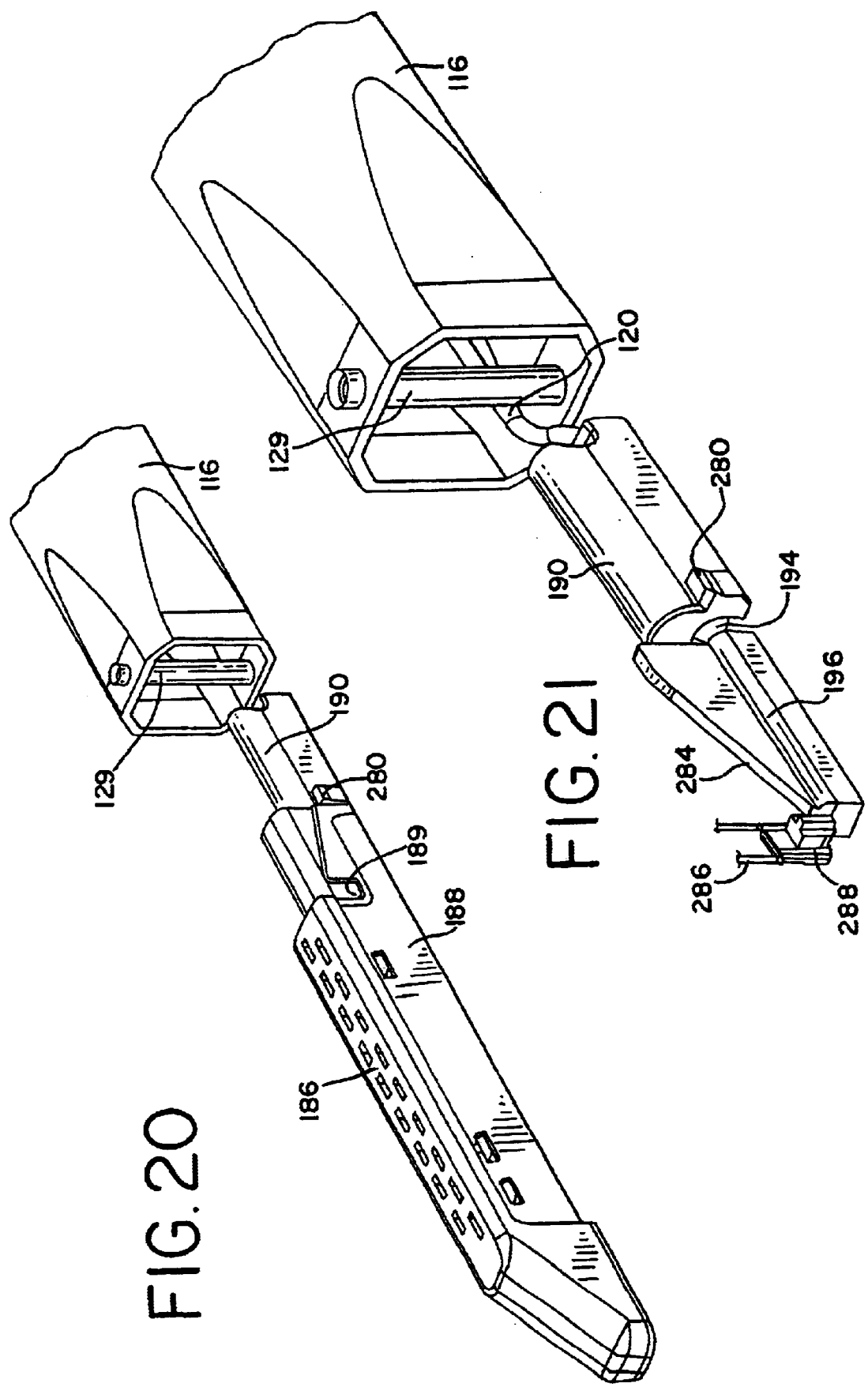

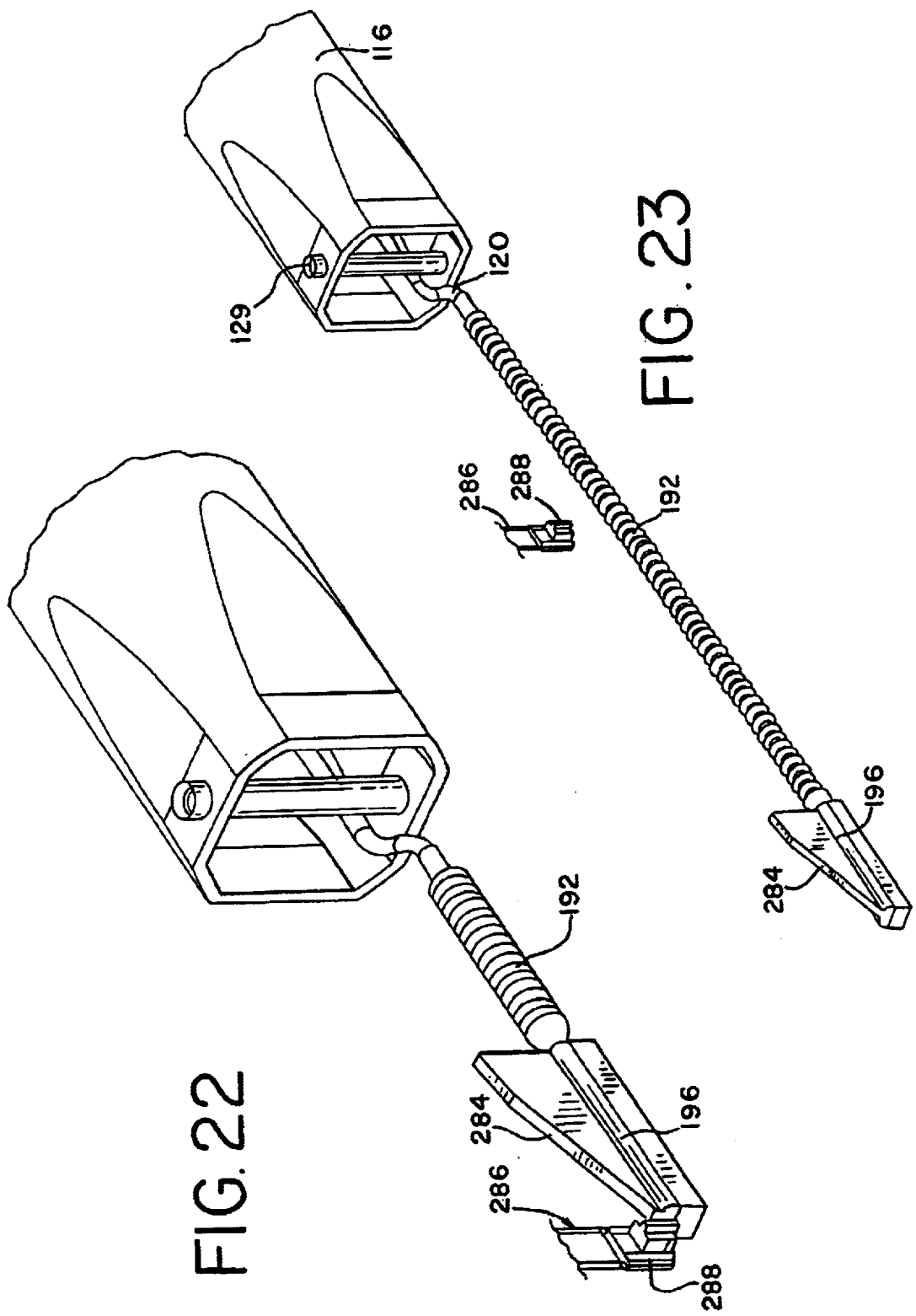

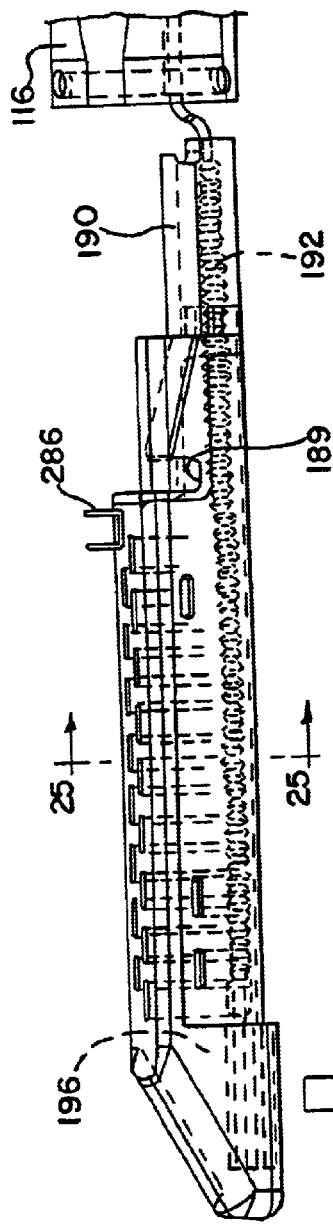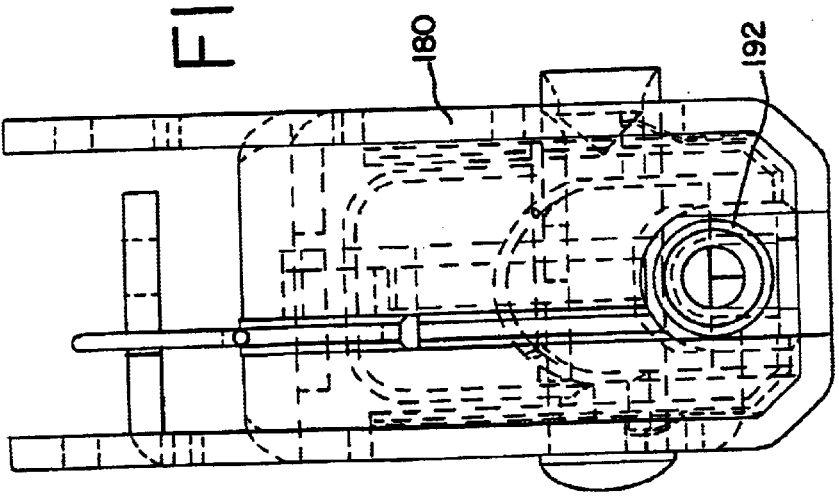

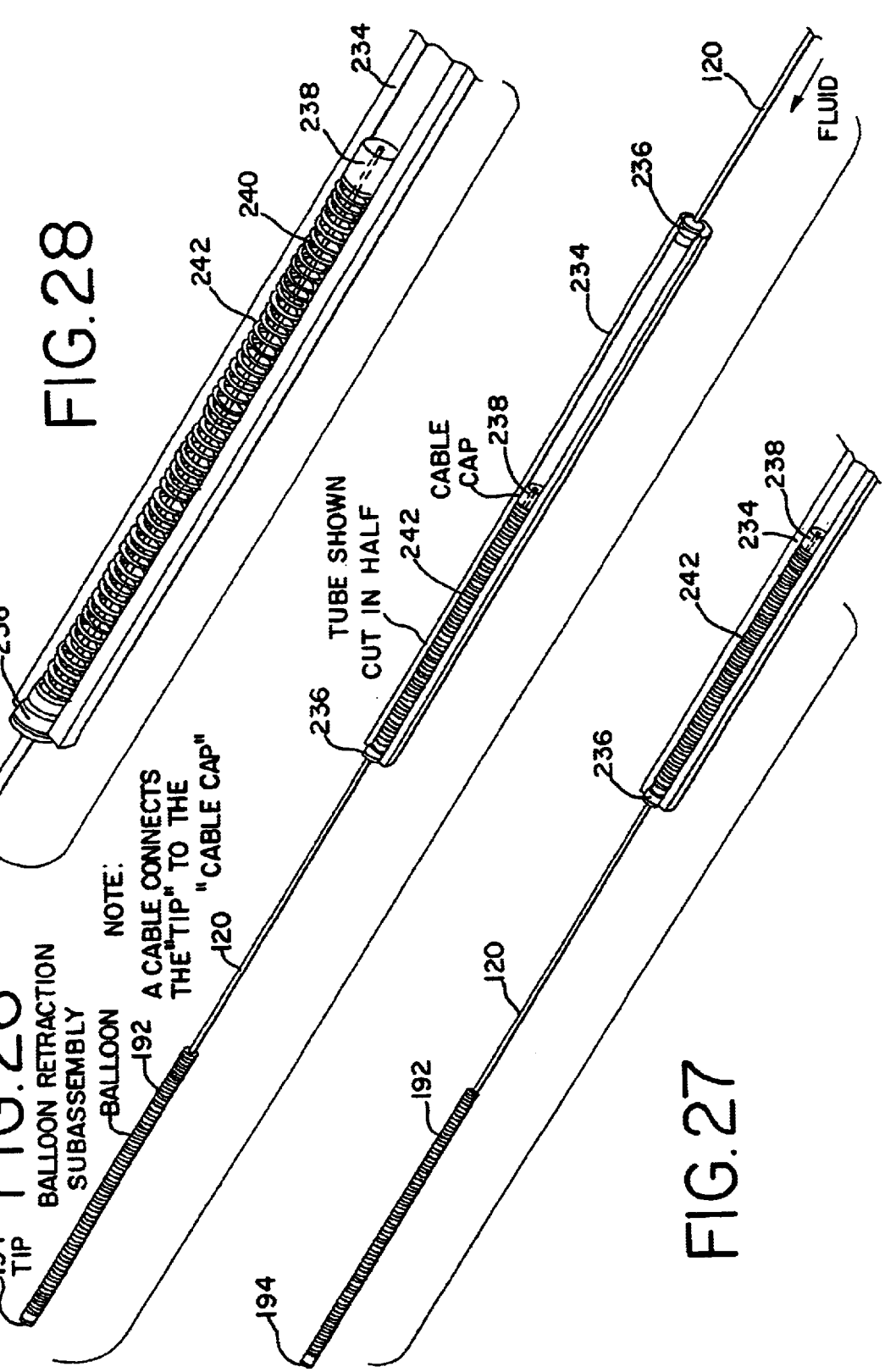

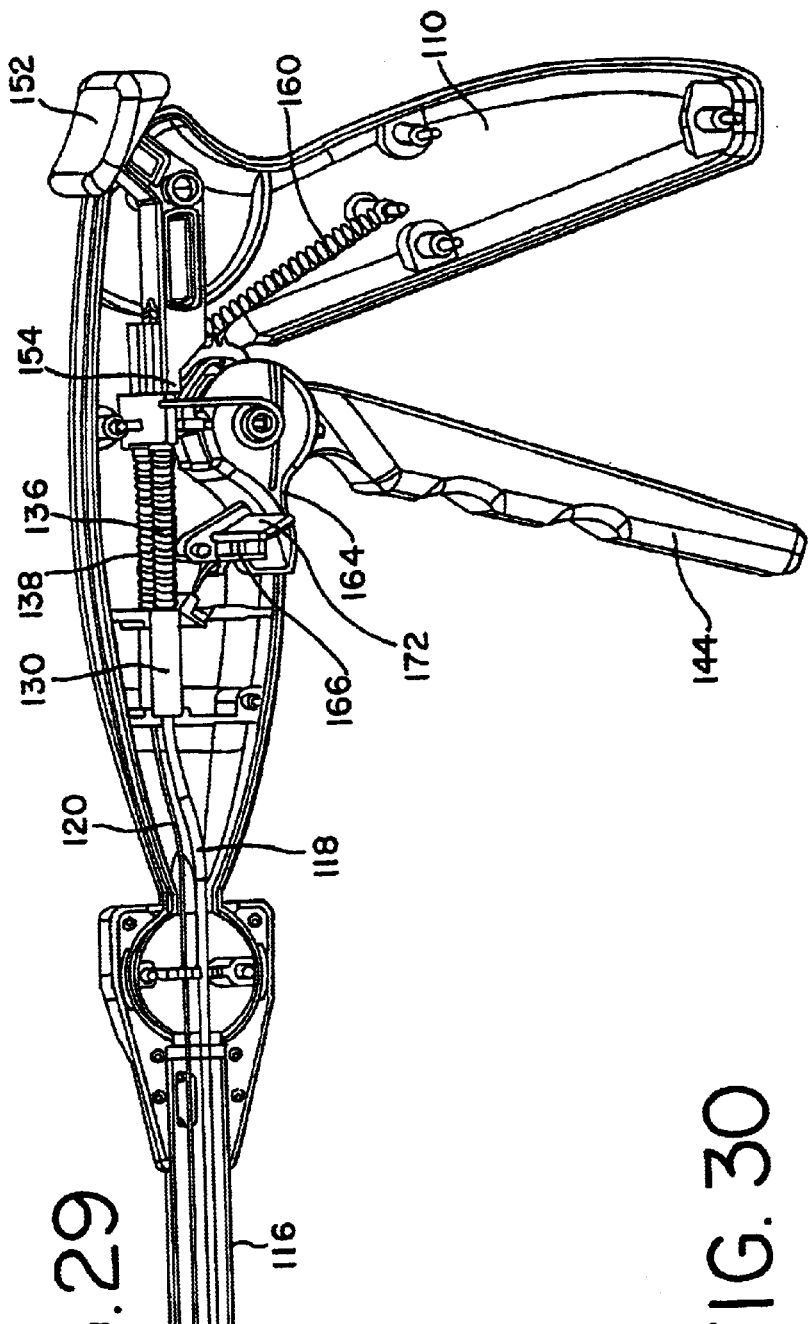
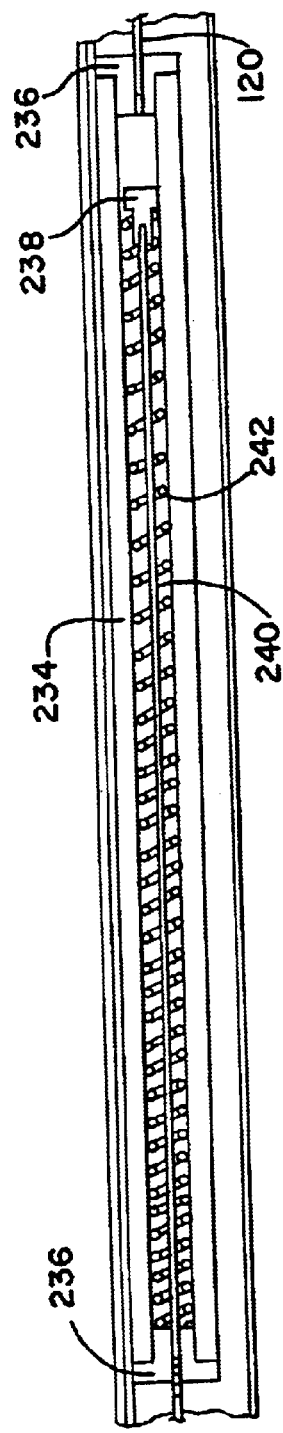
FIG. 29
FIG. 30

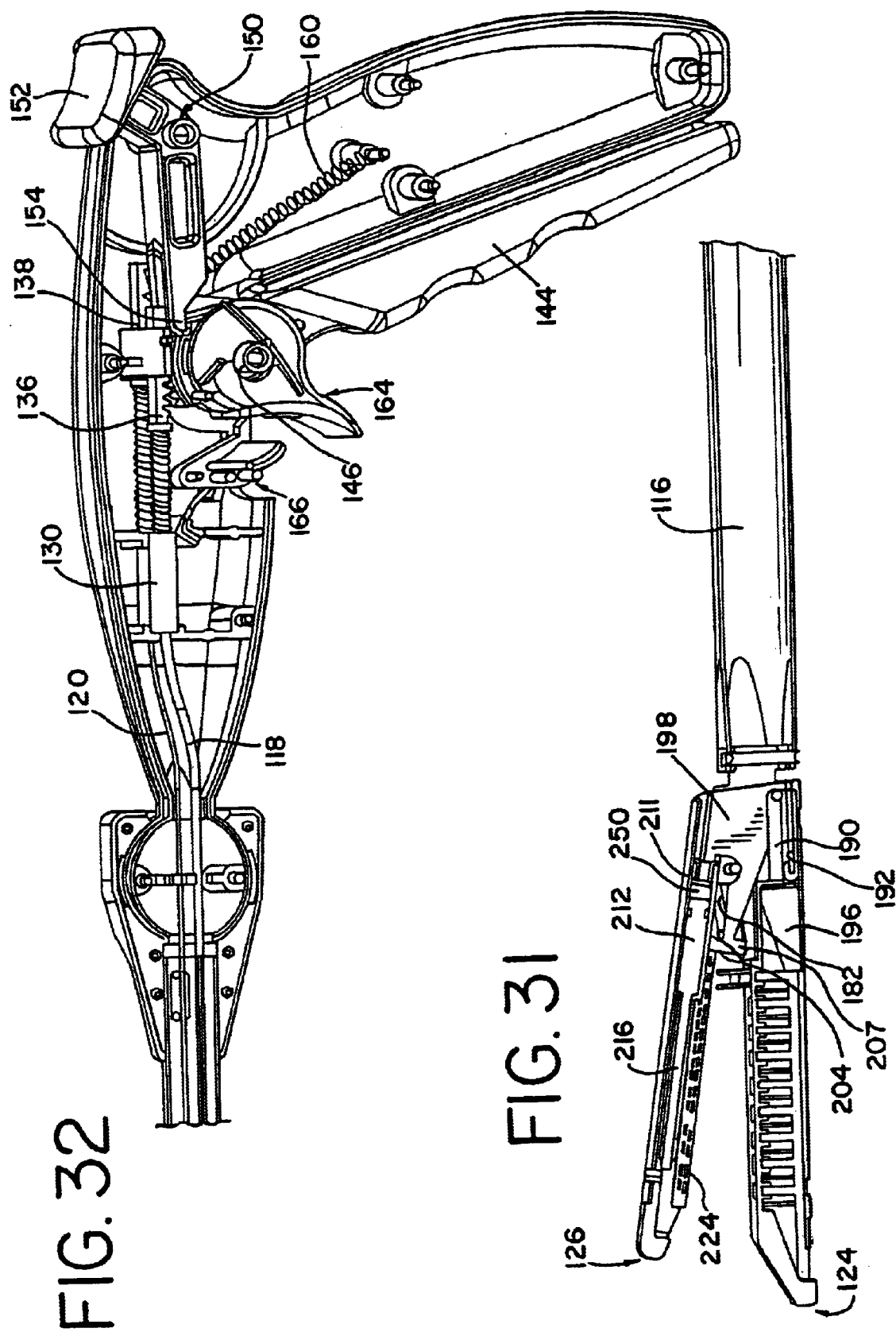

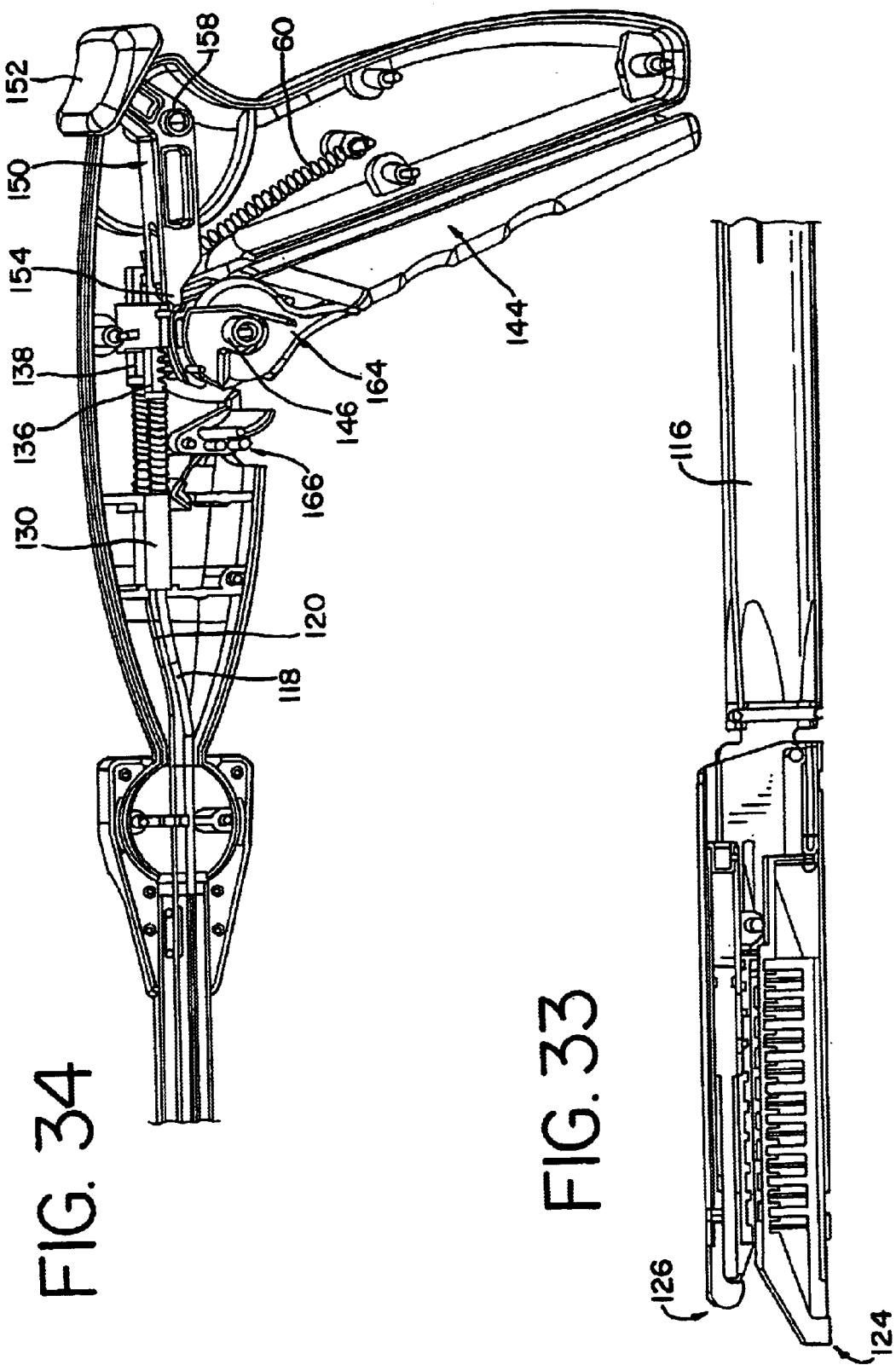

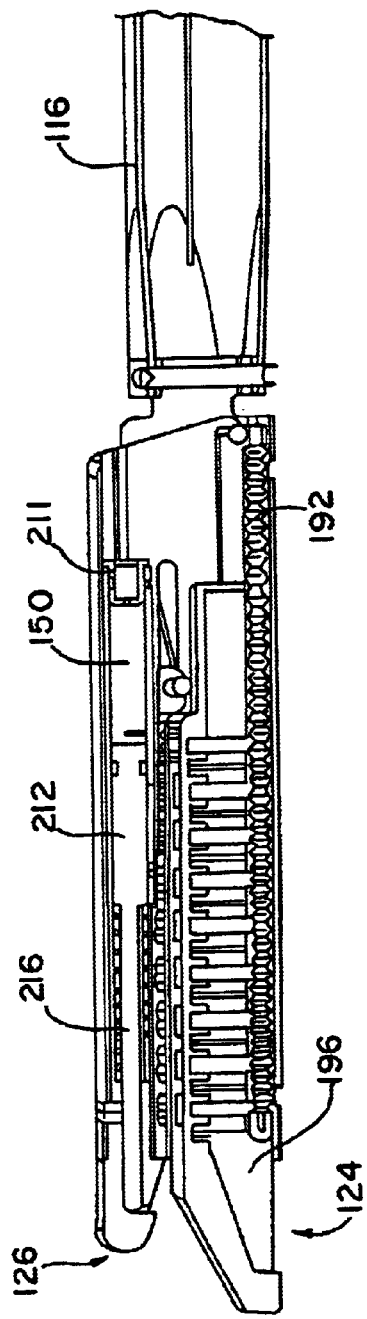
FIG. 35
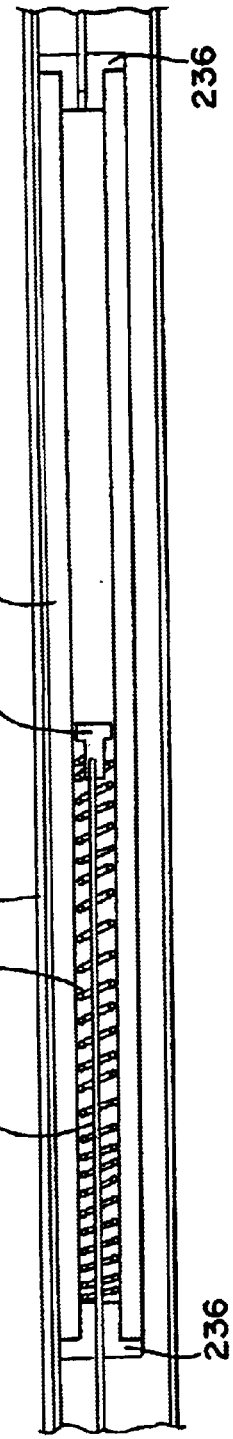
FIG. 36
FIG. 38 (RETRACTED, DEFLATED POSITION)
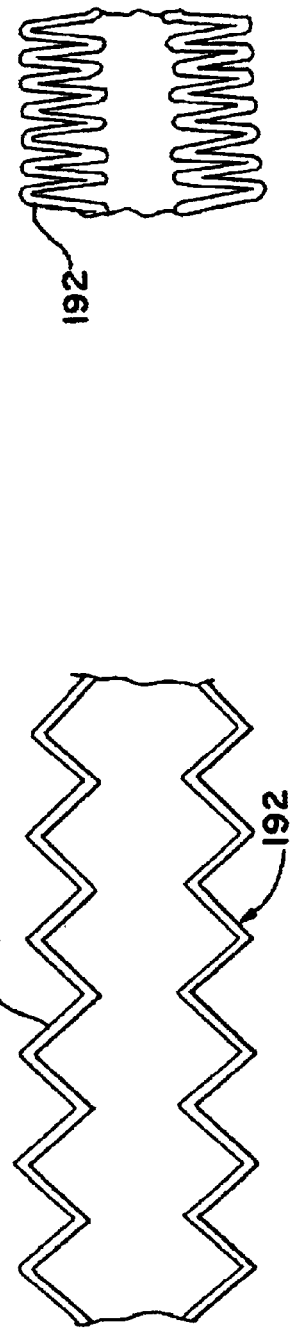
FIG. 37 (EXTENDED, INFLATED POSITION)

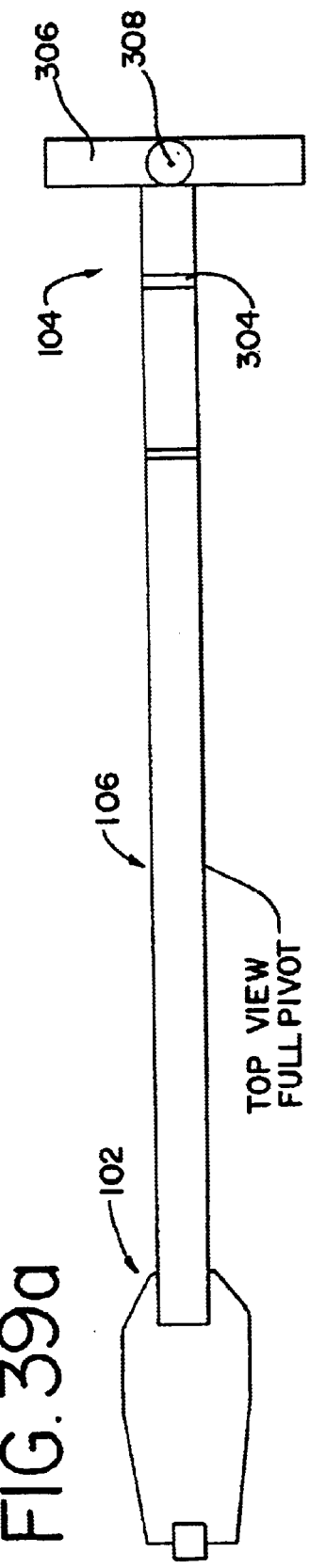
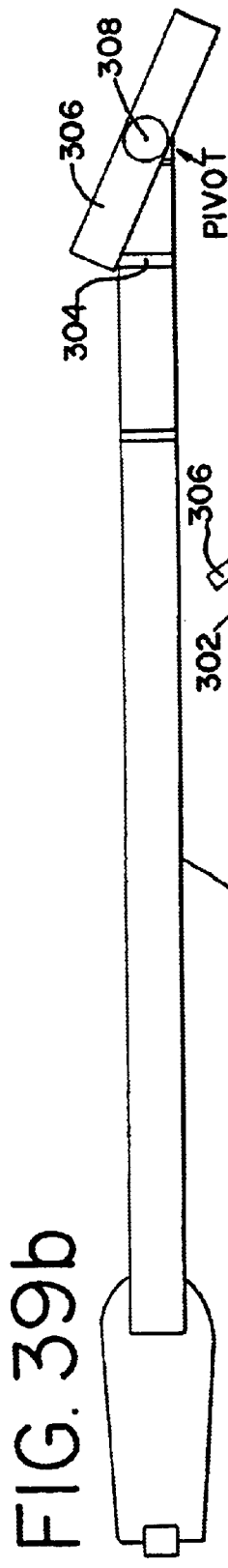
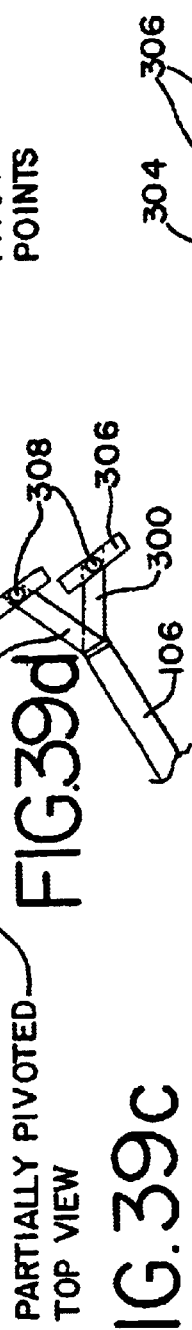
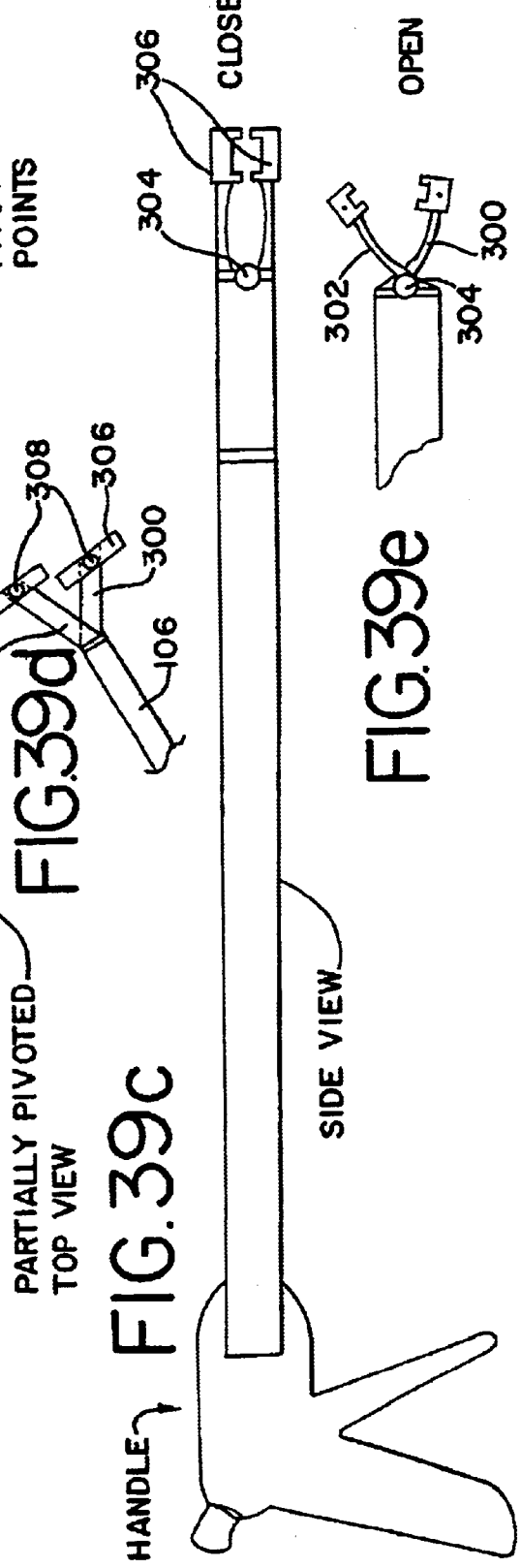
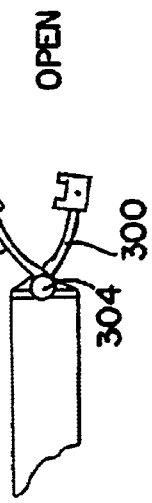
FIG. 39a TOP VIEW FULL PIVOT
FIG. 39b PARTIALLY PIVOTED TOP VIEW
FIG. 39c SIDE VIEW
FIG. 39d
FIG. 39e

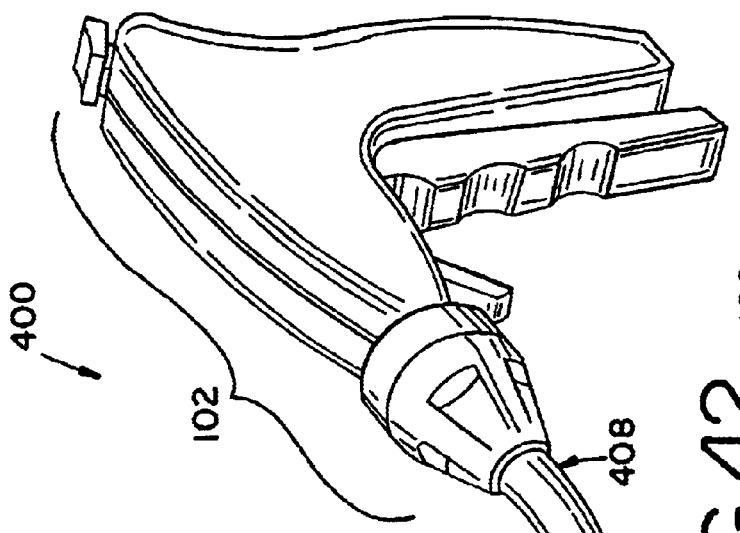
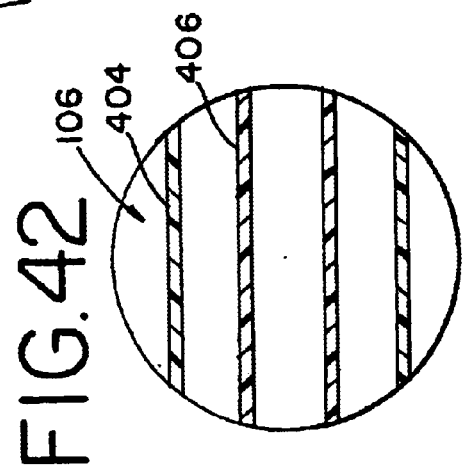
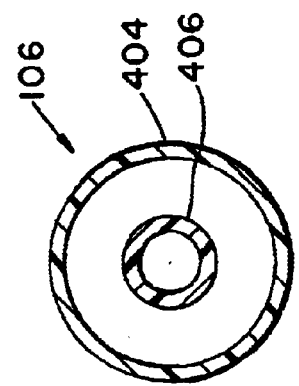
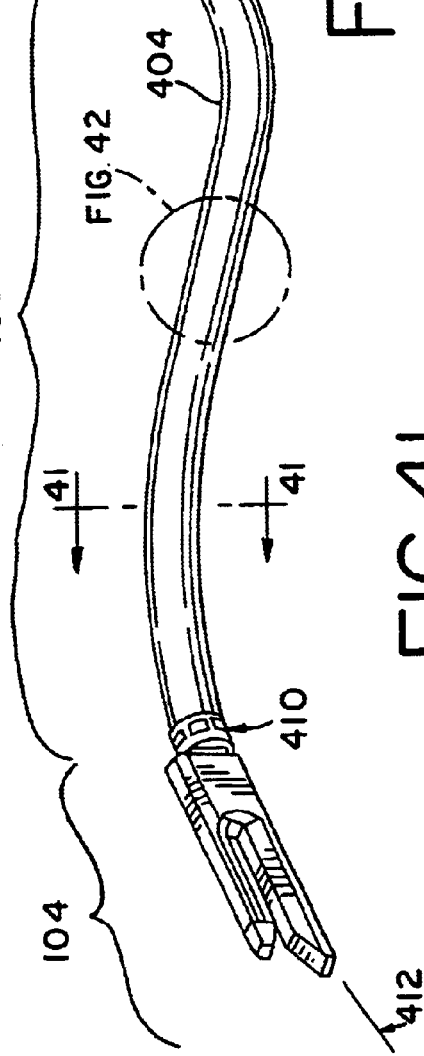
FIG. 40
FIG. 41
FIG. 42

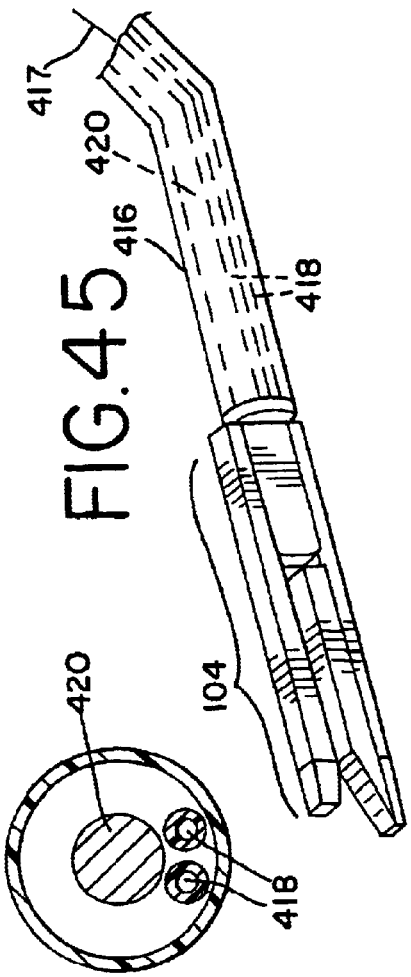
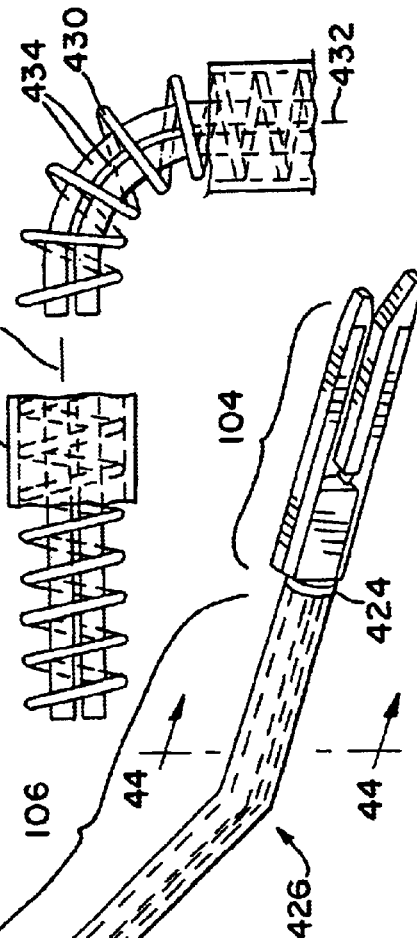

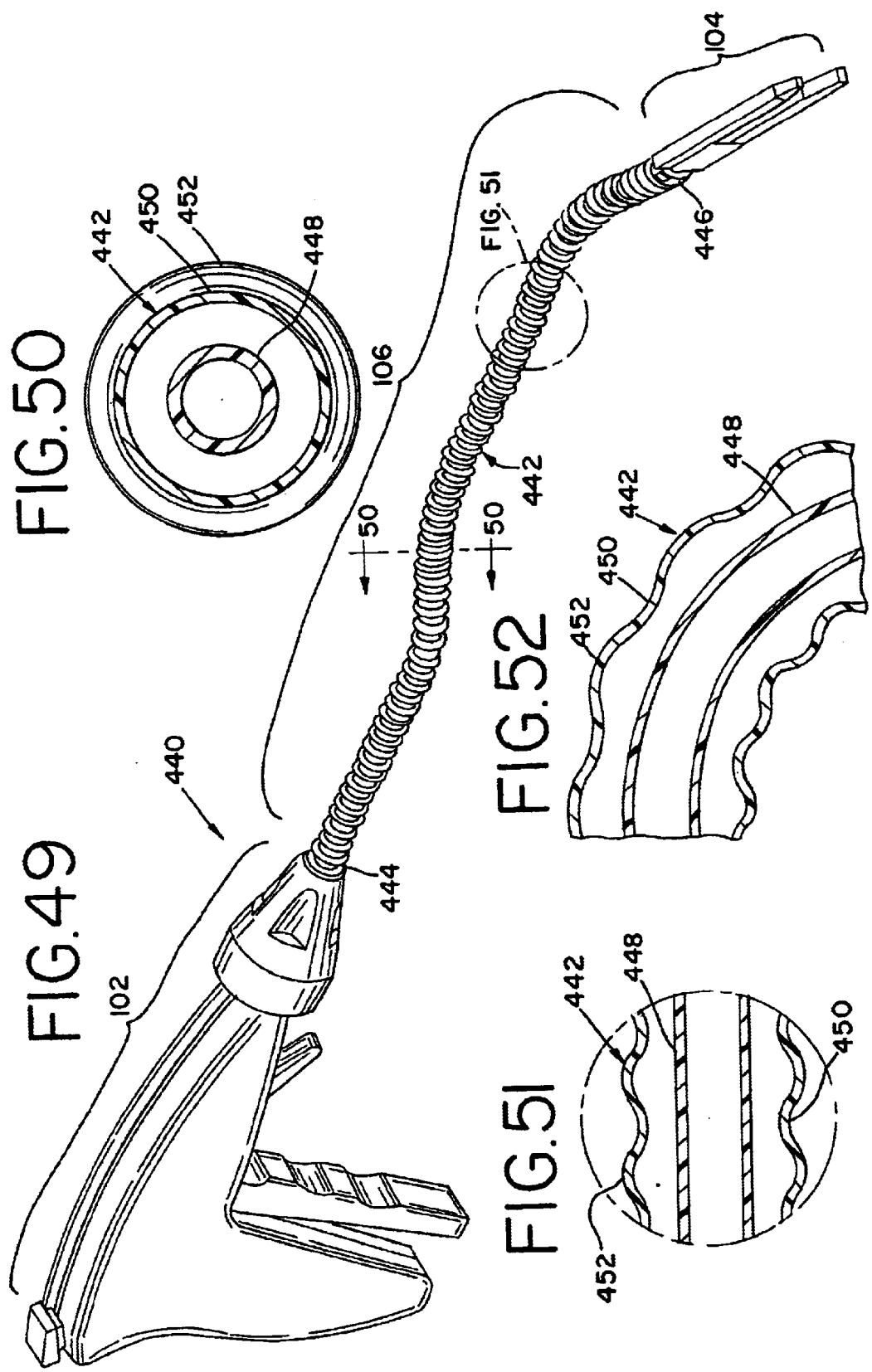

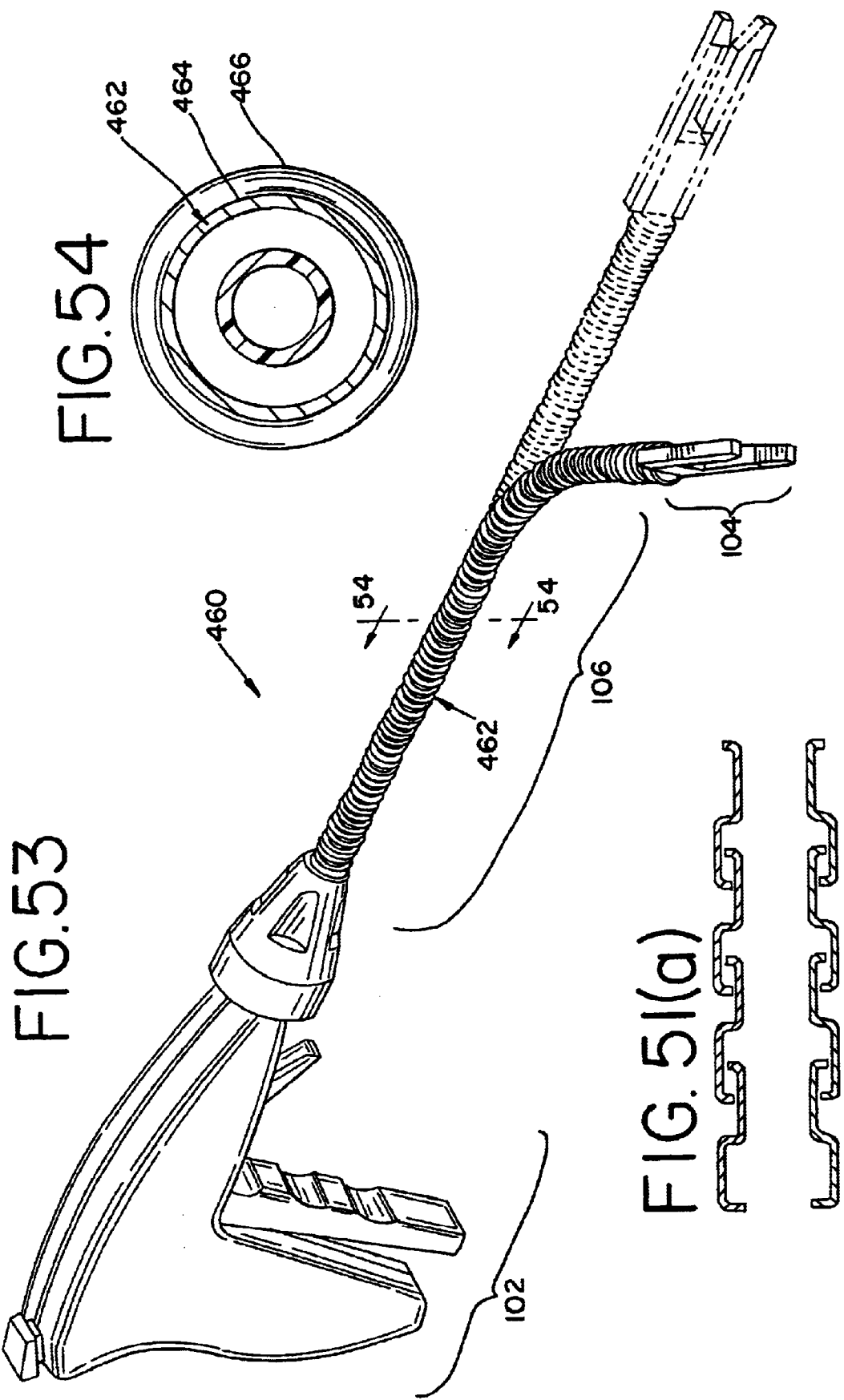

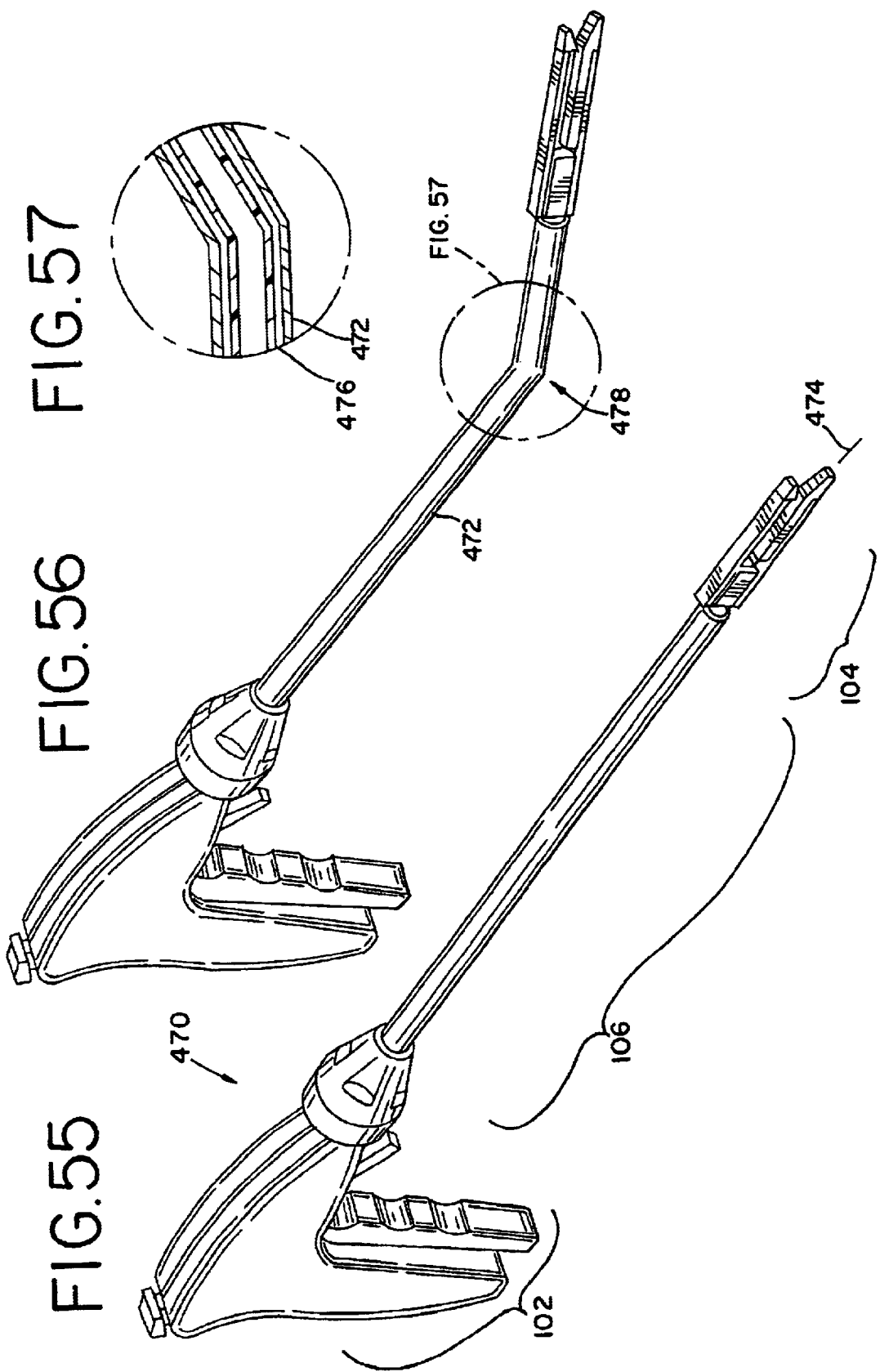

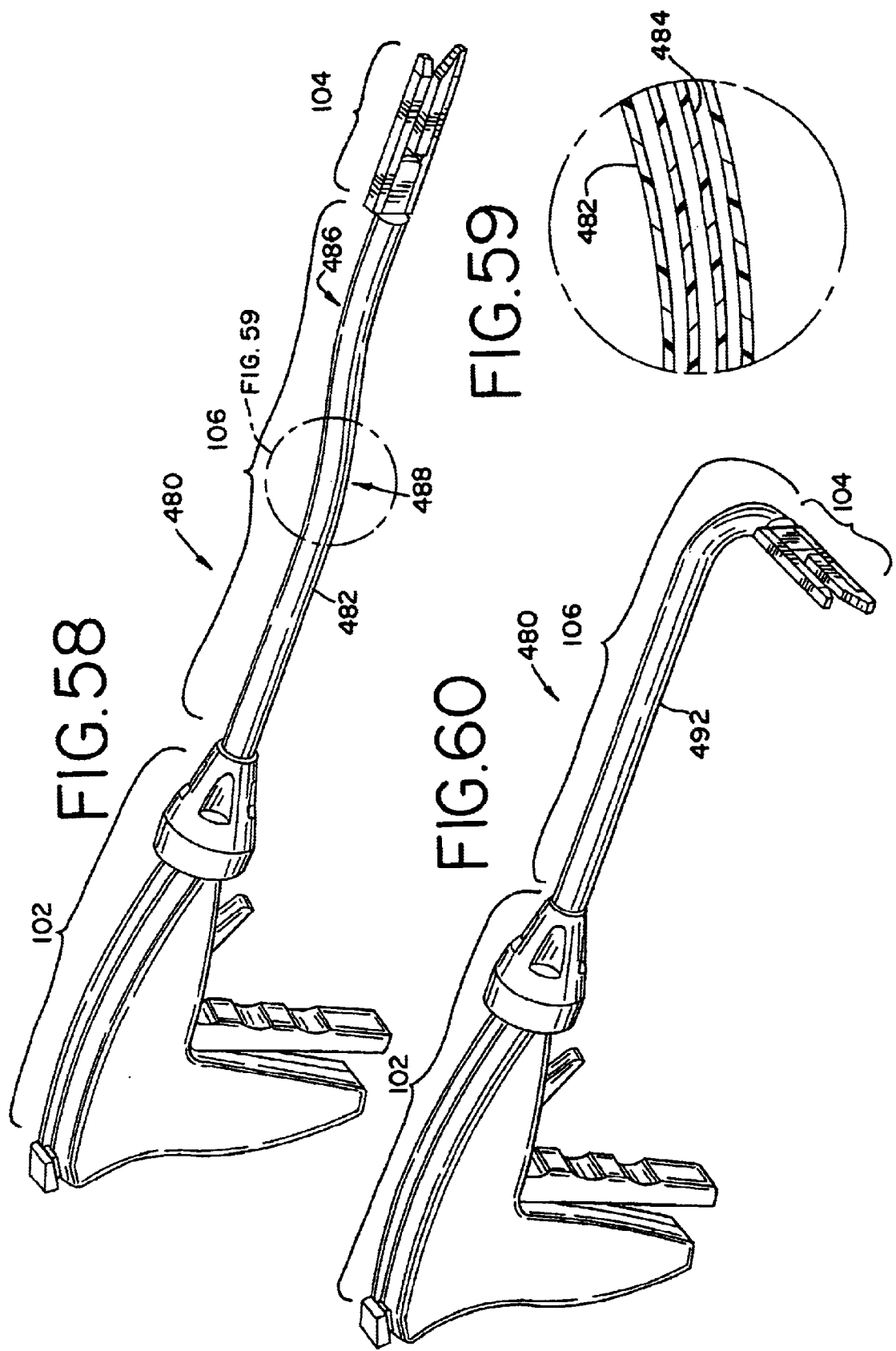

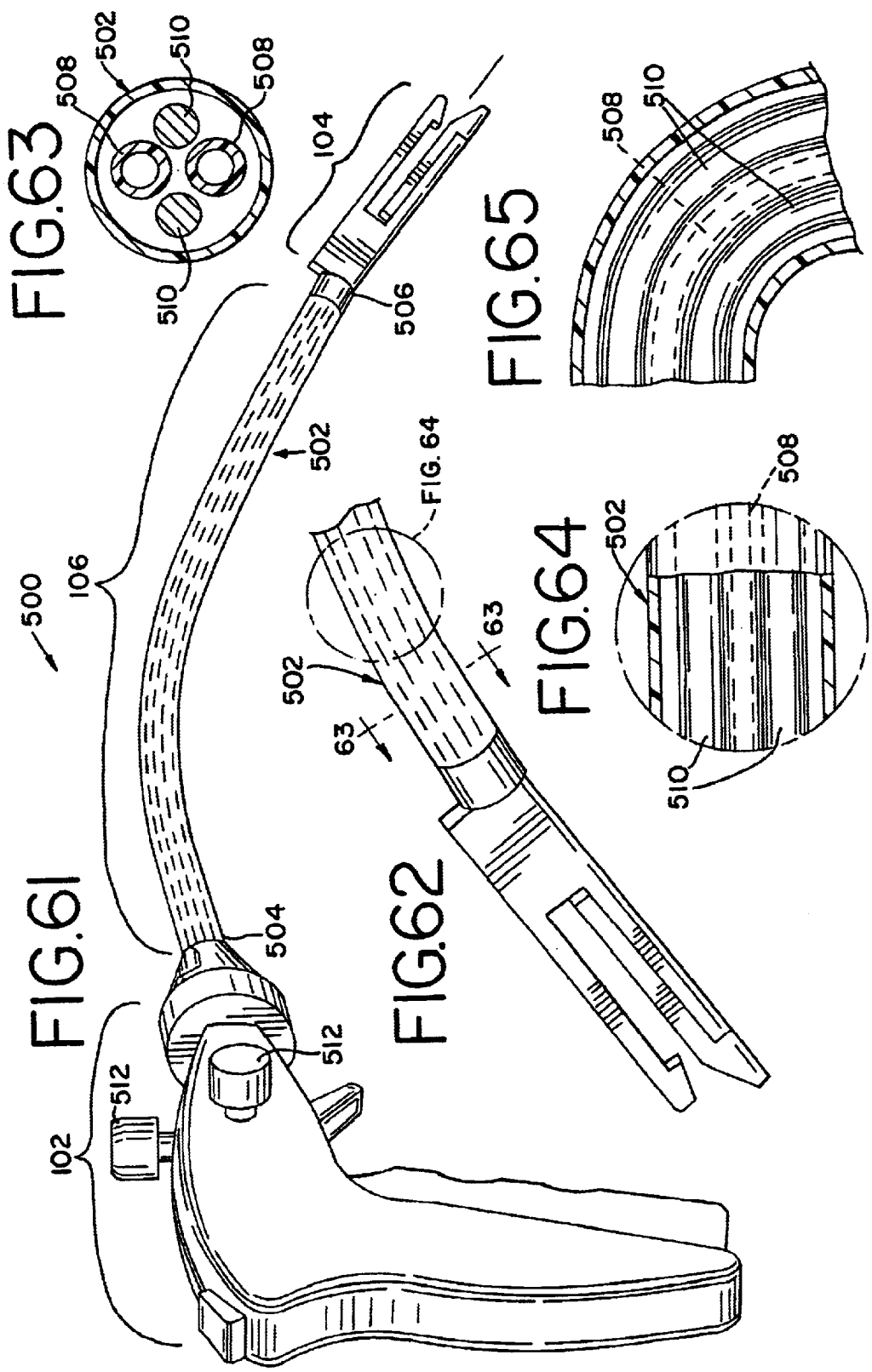

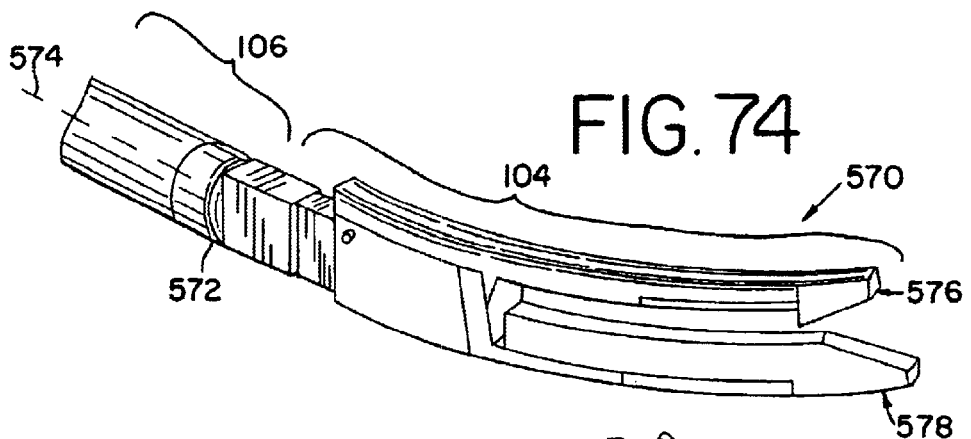
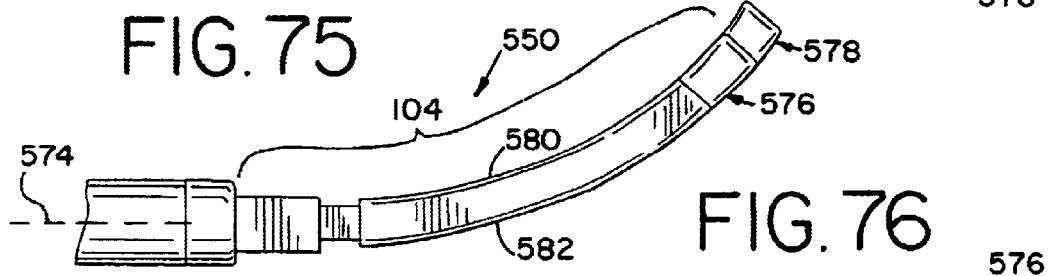
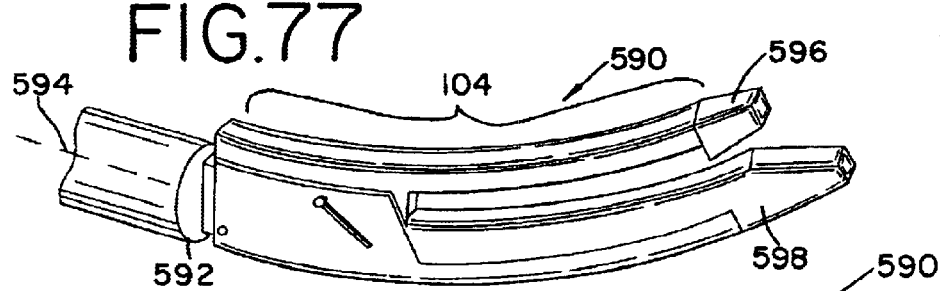
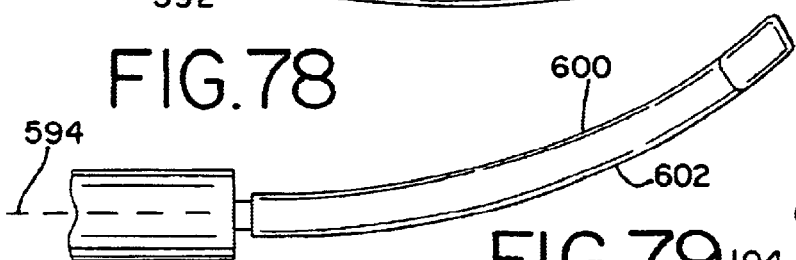
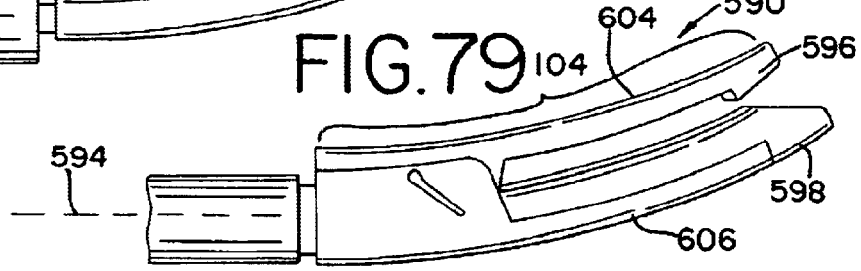

MEDICAL INSTRUMENT

PRIORITY CLAIM

This is a continuation-in-part application of U.S. patent application Ser. No. 09/942,236 which was filed on Aug. 29, 2001, to which this application claims priority.

BACKGROUND OF THE CLAIMED INVENTION

The present invention relates in general to medical instruments suitable for endoscopic or laproscopic applications, and capable of passing through a trocar or similar device. More specifically, the present invention relates to a novel hydraulically actuated medical instrument suitable for stapling or other desired endoscopic or laproscopic applications.

Surgical instruments, such as staplers, graspers, scissors, coagulators and the like, suitable for endoscopic or laproscopic applications in which the device is inserted through a cannula or trocar, are well known. As described in more detail below, the present invention, in its most preferred embodiment, is directed to an endoscopic stapler particularly suited for minimally invasive surgery, such as for isolating the left atrial appendage on human hearts. Such procedures are described in U.S. Pat. No. 5,306,234, and U.S. patent application Ser. No. 09/315,601, filed on May 20, 1999 to Aaron V. Kaplan, both of which are incorporated by reference herein.

Also, endoscopic medical instruments are often of complicated construction, especially when the instrument is articulated to allow the handle and/or end effector to pivot or rotate. Typically, a mechanical linkage extends between the handle and end effector to allow operator actuation of the end effector. When the instrument is of the type that permits articulation, the mechanical linkage must accommodate the articulation. This often results in a design that is relatively complicated, that is costly to manufacture and/or that may still experience limitations regarding the degree or direction of articulation.

The mechanical linkage also may limit the shape, or configuration of the shaft and/or the ability of the shaft to be flexible so as to navigate a path within the body cavity during the medical procedure.

Other complications of a mechanical linkage may also arise relative to the shape and configuration of the end effector. The mechanical linkage must interface with the end effector so as to permit relative movement of the jaws in addition to driving of the staples. This can result in a complex attachment between the end effector and mechanical linkage that is expensive to make and difficult to assemble.

SUMMARY OF THE CLAIMED INVENTION

The present invention may be generally embodied in a hydraulically actuated medical device of a type suitable for endoscopic or laproscopic procedures and which includes, in one embodiment, an elongated shaft having a proximal end and a distal end, an end effector at the distal end of the elongated shaft, a handle portion at the proximal end of the elongated shaft, and a fluid flow path extending between the handle and the end effector.

In accordance with one aspect of the present invention, the end effector is elongated and at least a portion of the end effector extends at an angle to another portion of the end effector to make the end effector suitable for particular procedures. For example, the end effector may be continuously curved along its length so as to contact the tissue that is being stapled or otherwise treated in an arc. Any curved configuration of the end effector, such as lateral, vertical or complex, is contemplated by the present invention and intended to be within the above reference to one portion of the end effector extending to an angle to another portion. Also, the end effector may have at least two straight portions, one of which extends at a fixed or variable angle to the other portions.

It is possible for the end effector to be flexible along its entire length or a portion thereof and/or to employ suitable inner malleable shape-retaining elements. The end effector may be made of any polymer or metallic substance or other suitable materials as well as a combination thereof. The end effector is preferably preformed to exhibit a desired configuration corresponding to a specific medical procedure.

In accordance with another aspect of the present invention, at least a portion of the shaft may be flexible so that the shaft may be manually configured into a particular non-straight shape (such as a curved, offset, fixed or variable angle), which one portion of the shaft extends at an angle relative to another portion. The shaft may be flexible along its entire length or a substantial portion thereof to provide for a variety of shapes and configurations of the shaft, as will be described below.

In accordance with a further aspect of the present invention, the elongated shaft may include a flexible outer shaft having at least one inner hydraulic fluid flow path extending between the handle portion and the end effector through the elongated shaft. At least a portion of the shaft is manually movable to a direction in which it extends at an angle to another portion of the shaft. It is contemplated that numerous shapes and configurations of the shaft are possible and may depend on the particular medical procedure employed, the area of the body involved in the medical procedure, and the method of approach utilized as well as other factors.

The shaft may be flexible along its entire length or any portion thereof. The shaft may be resilient, have shape retaining characteristics or it may be capable of freely conforming to the shape configuration of the pathway defined by its surroundings such as, for example, a trocar, introduction sleeve or a channel defined within the patient. Where the shaft is capable of shape retention, the shape and configuration of the shaft may be deformed, for example, manually by the operator, and the shape is retained until repositioned or, alternately, via control wires extending from the handle, through the shaft which can control the direction, shape and configuration of the shaft.

The shaft may be comprised of a suitable plastic polymeric material, metal, other suitable materials or a combination thereof. The material may also be manufactured into a preformed configuration using heat-forming techniques such as, for example, thermoforming which allows a shaft made of plastic in part or in whole to be preformed into a particular shape or corresponding to a specific medical procedure. Other methods may also be used, such as conventional shape forming methods, to form metallic materials into a particular shape. The outer shaft also may have a generally fluted, accordion, corrugated or undulating shape-retaining surface.

In another aspect of the present invention the shaft may be comprised of an outer flexible shaft and an inner metallic element extending along the shaft between the handle portion and the end effector. The inner malleable element preferably is capable of shape retention and can be manually moved or deformed into a desired configuration where at least a portion of the shaft extends at an angled direction relative to another portion of the shaft. Manual movement allows deflection or angling of the shaft along one or more portions of the shaft and is preferably provided at the distal portion of the shaft which is inserted into the patient's body. Manual movement can be effectuated in one or more planes relative to the longitudinal axis of the shaft. The shape and configuration of the shaft may be set, for example, directly by hand or indirectly using control rods. It is contemplated that the metallic element may be in the form of, for example, a metal rod, a spiral wound wire, as well as other malleable shape retention members or configurations.

Other features and aspects of the present invention are set forth in the following detailed description and claims.

DESCRIPTION OF DRAWINGS

FIG. 18 is a perspective view of the end effector jaws of the instrument of FIG. 1 in the closed position.

FIG. 19 is a perspective view of the lower end effector jaw of the present invention in FIG. 18, with the upper jaw removed.

FIG. 20 is a perspective view of the lower jaw of the end effector, with portions removed as compared to FIG. 19 for better illustration.

FIG. 21 is a perspective view of portions of the lower end effector jaw, with portions removed as compared to FIG. 20 for better illustration.

FIG. 22 is a perspective view of portions of the lower end effector jaw with portions removed as compared to FIG. 21 for better illustration.

FIG. 23 is a perspective view of portions of the lower end effector jaw, comparable to FIG. 22, but with the balloon expanded to illustrate the balloon position after staple firing.

FIG. 24 is a side view of the lower end effector jaw after staple firing.

FIG. 25 is a vertical cross-sectional view taken along lines 25—25 of FIG. 24.

FIG. 26 is a perspective view of a portion of the balloon retraction assembly of the instrument of FIG. 1 for retracting the balloon after staple firing.

FIG. 27 is an enlarged view of a portion of the distal portion of FIG. 26, for better illustration of the balloon and parts of the balloon retraction assembly.

FIG. 28 is a further enlarged view of a portion of the balloon retraction of assembly of FIG. 26.

FIG. 29 is an enlarged cross-sectional view of the handle portion and first articulation joint connecting the handle portion to the barrel portion of the instrument shown in FIG. 1, with the jaws of the end effector in an open position.

FIG. 30 is a cross-sectional view of a barrel portion of the instrument of FIG. 1, illustrating a portion of the mechanism for positively retracting the actuator balloon after staple firing. The position indicated in FIG. 30 is the position with the balloon fully retracted before staple firing.

FIG. 31 is an enlarged cross-sectional view of the end effector portion and distal end of the barrel portion of the instrument of FIG. 1, showing the jaws in the fully open position.

FIG. 32 is an enlarged cross-sectional view of the handle portion and first articulation joint or gimbal connecting the handle portion to the barrel portion of the instrument shown in FIG. 1 with the jaws of the end effector in a closed position.

FIG. 33 is an enlarged cross-sectional view of the end effector portion and distal end of the barrel portion of the instrument of FIG. 1 showing the jaws in the fully clamped position.

FIG. 34 is an enlarged cross-sectional view of the handle portion and first articulation joint or gimbal connecting the handle portion to the barrel portion of the instrument shown in FIG. 1 with the jaws of the end effector in a closed position and the staples fired.

FIG. 35 is an enlarged cross-sectional view of the end effector portion and distal end of the barrel portion of the instrument of FIG. 1 showing the jaws in the fully clamped position and staples fired.

FIG. 36 is a cross-sectional view of a barrel portion of the instrument of FIG. 1, illustrating a portion of the mechanism for positively retracting the actuator balloon after staple firing. The position indicated in FIG. 36 is the position with the balloon expanded to its full length after staple firing.

FIGS. 37 and 38 are cross-sectional views, respectively, of the staple actuation balloon in the inflated and deflated condition.

FIG. 39a is a top view of an instrument of the present invention employing distal jaws that are pivotable in different directions, and showing the jaws pivoted at a right angle to the barrel.

FIG. 39b is a top view of the instrument of FIG. 39a with the jaws pivoted at less than 90° to the barrel.

FIG. 39c is a side view of the instrument of FIG. 39a with the jaws closed.

FIG. 39d is a perspective view of the distal end of the instrument of FIG. 39b.

FIG. 39e is a side view of the distal end of the instrument of FIG. 39c with the jaws open.

FIG. 40 is a perspective view of an instrument of the present invention employing a flexible outer shaft.

FIG. 41 is an enlarged cross-sectional view of the shaft of FIG. 40 along line 41—41.

FIG. 42 is an enlarged longitudinal section of the shaft in FIG. 40 of the indicated encircled area.

FIG. 43 is a perspective view of a medical instrument employing an inner malleable element extending within the shaft.

FIG. 44 is an enlarged sectional view of the shaft in FIG. 40 along line 44—44.

FIG. 45 is an enlarged perspective view of the distal end portion of FIG. 43.

FIG. 46 is an enlarged partial perspective view of the shaft with portions of the shaft shown removed.

FIG. 47 is an enlarged partial elevational view of a shaft, with portions of the shaft shown removed, employing an alternate inner malleable element.

FIG. 48 is an enlarged partial elevational view of the shaft in FIG. 47 shown in an angled configuration.

FIG. 49 is a perspective view of an instrument employing an accordion or corrugated shape-retaining shaft.

FIG. 50 is an enlarged cross-sectional view of FIG. 49 along line 50—50.

FIG. 51 is an enlarged longitudinal section of FIG. 49 of the indicated encircled area.

FIG. 51a illustrates an enlarged partial longitudinal cross-section of an alternate shaft configuration which shows overlapping tubular sections in a similar manner as used with BX cable.

FIG. 52 is a similar view of the shaft as shown in FIG. 51 except the shaft in FIG. 52 is shown in an angled configuration.

FIG. 53 is a perspective view of an instrument comprising a corrugated shape retaining shaft.

FIG. 54 is an enlarged cross-sectional view of FIG. 53 along line 54—54.

FIG. 55 is a perspective view of an instrument having a metallic shape retaining shaft.

FIG. 56 is a perspective view of the instrument shown in FIG. 55 except that FIG. 56 illustrates the shaft having an angled configuration.

FIG. 57 is an enlarged longitudinal section of FIG. 56 of the indicated encircled area.

FIG. 58 is a perspective view of an instrument including a shaft having a preformed angled configuration.

FIG. 59 is an enlarged longitudinal section of FIG. 58 of the indicated encircled area.

FIG. 60 is a perspective view of an instrument having an alternate preformed configuration of its shaft.

FIG. 61 is a perspective view of an instrument which includes a shaft having control rods extending along the shaft.

FIG. 62 is an enlarged perspective view of the distal portion of the instrument in FIG. 61.

FIG. 63 is an enlarged sectional view of the shaft of FIG. 62 along line 63—63.

FIG. 64 is an enlarged longitudinal section of the shaft shown in FIG. 62 of the indicated encircled area as viewed from above.

FIG. 65 illustrates a view similar to that shown in FIG. 64 except that FIG. 65 illustrates the shaft in an angled configuration.

FIG. 74 is a perspective view of the distal portion of an instrument having an end effector which is curved in a horizontal direction relative to a longitudinal shaft axis such that one portion of the end effector extends at an angle relative to another portion.

FIG. 75 is a top view of the end effector of FIG. 74.

FIG. 76 is a side elevational view of FIG. 74.

FIG. 77 is a perspective view of the distal portion of and instrument employing an end effector which is curved in both the vertical and horizontal directions relative to a longitudinal shaft axis such that one portion of the end effector extends at an angle relative to another portion.

FIG. 78 is a top view of FIG. 77.

FIG. 79 is a side elevational view of FIG. 77.

DESCRIPTION OF ILLUSTRATED INSTRUMENT

Figure 1:
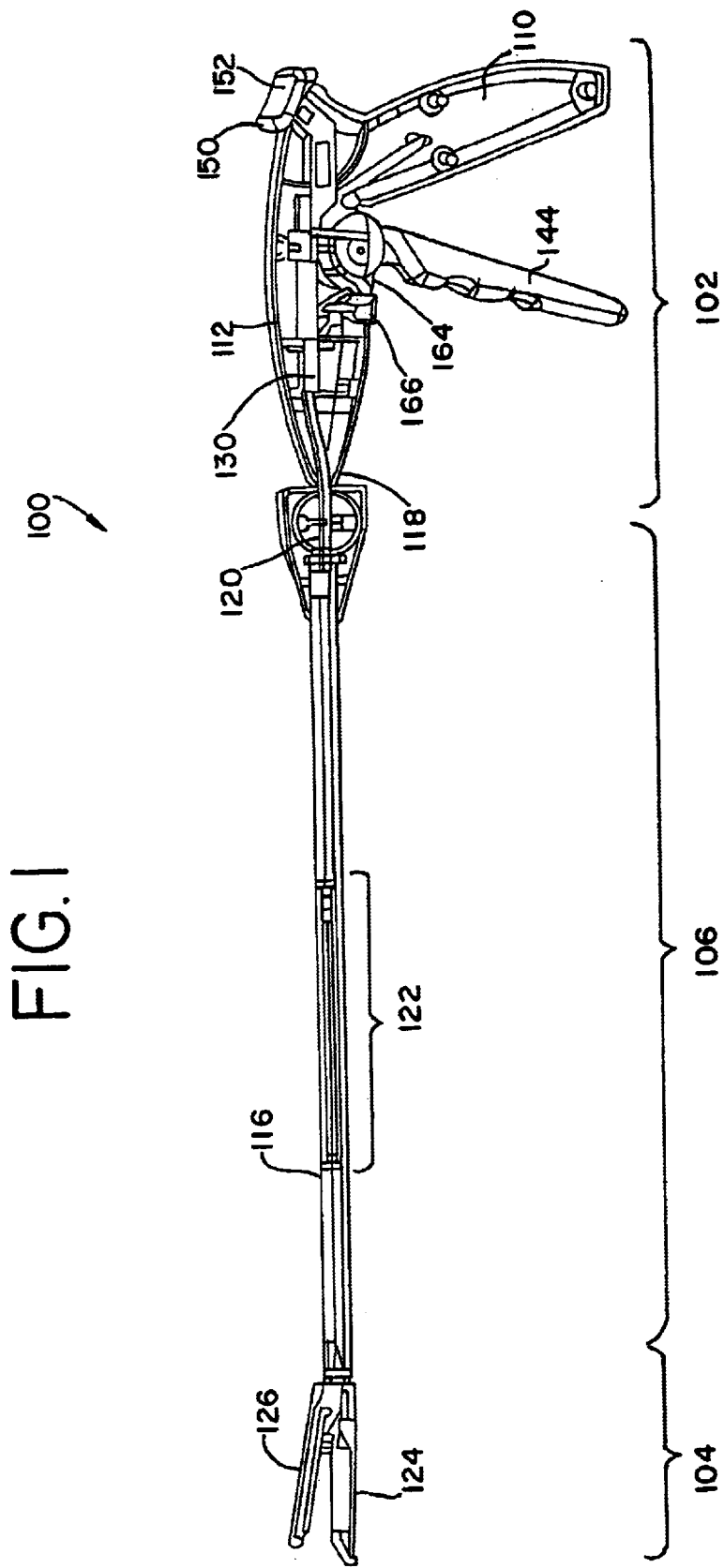
FIG. 1 is vertical cross-sectional view of an endoscopic stapling instrument employing the various features and aspects of the present invention. This figure shows the handle assembly, barrel or shaft assembly and end effector assembly. This cross-sectional view is slightly tilted toward the viewer to provide a slightly downward perspective.
Figure 2:
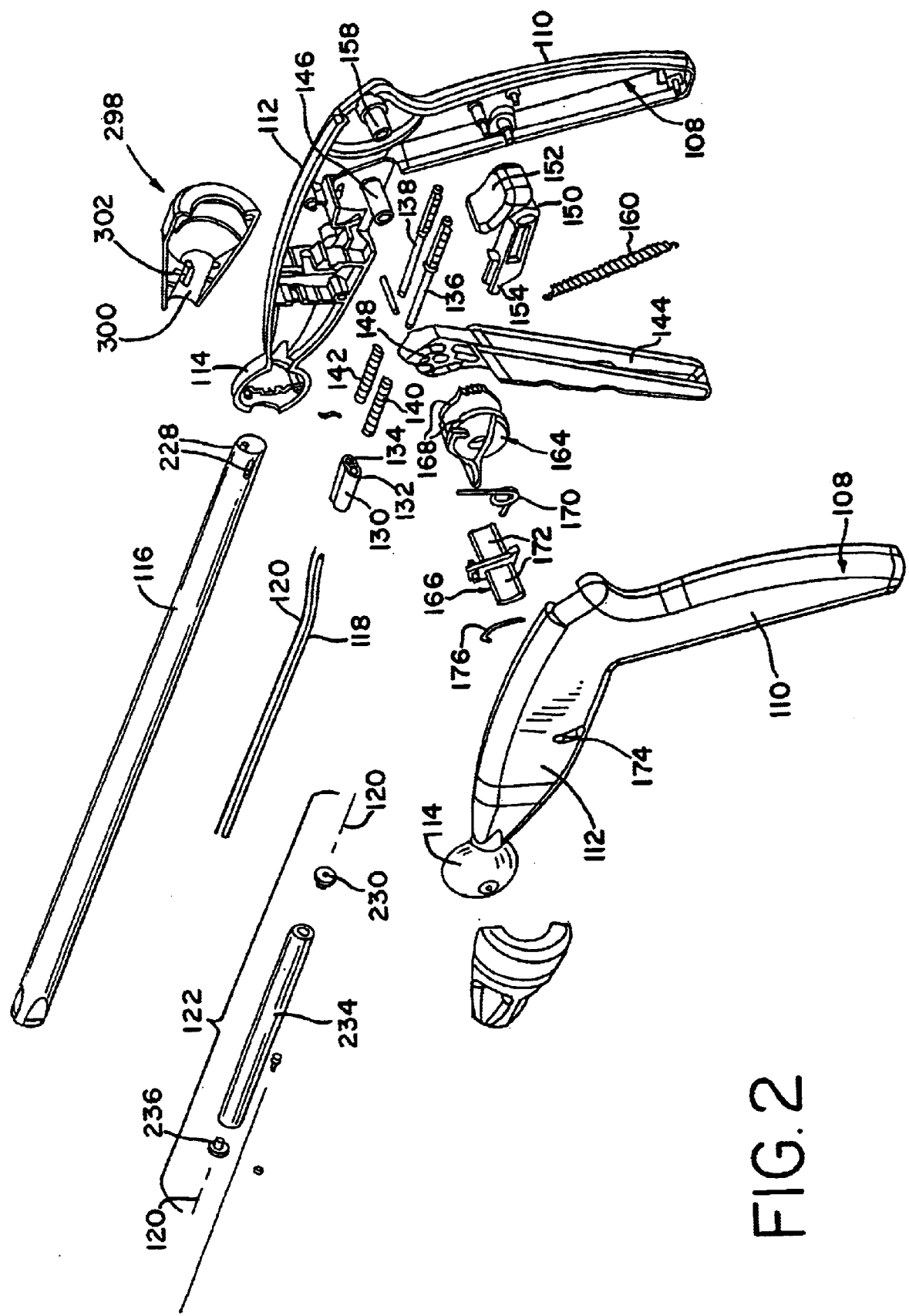
FIG. 2 is an exploded perspective view of the handle assembly and the barrel assembly of the instrument of FIG. 1.
Figure 3:
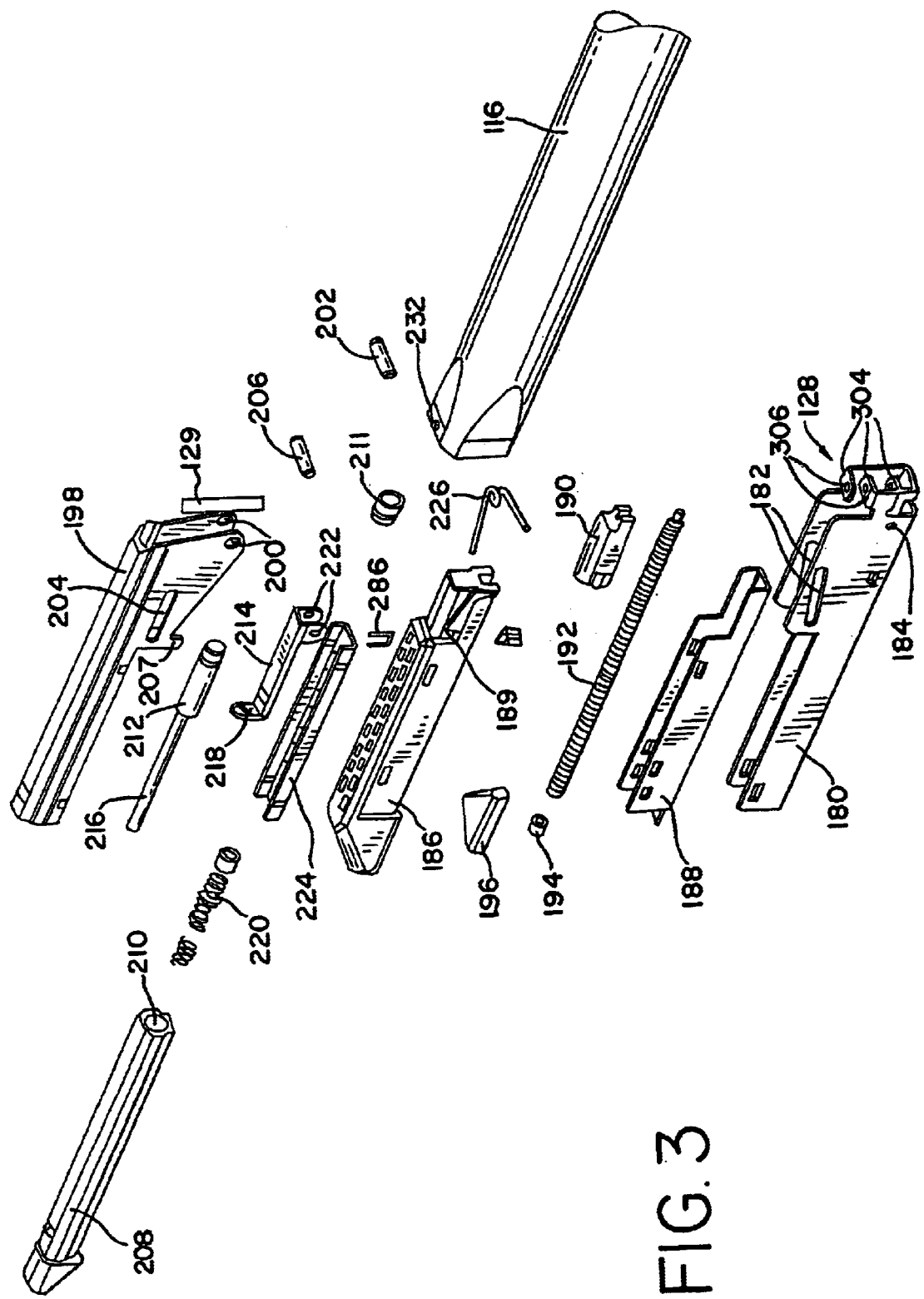
FIG. 3 is an exploded perspective view of the end effector assembly (the clamping and stapling jaws) of the instrument of FIG. 1.

FIG. 1 is an overall cross-sectional view of a surgical stapling instrument, generally at 100, particularly suited for endoscopic or laproscopic isolation of the left atrial appendage. As shown in FIGS. 1–3, the illustrated instrument 100 includes a proximal handle portion or assembly, generally at 102, a distal end effector or implement portion or assembly 104 and an intermediate barrel or shaft portion or assembly, generally at 106, connecting the handle and the effector portions. In this form, the present invention is particularly well suited for endoscopic application, where the end effector is inserted through a trocar or like device and is operated by the handle portion, which remains outside the patient.

Although the present invention is illustrated in the context of an endoscopic stapler, the present invention is not, in its broader aspects, limited to a stapler or to a particular type of end effector. Accordingly, it should be understood that the following description of the present invention in its present and preferred stapler construction is for the purposes of illustration, and not for the purposes of limiting various aspects of the present invention to the specific structure or form shown in the drawings.

Turning first to a brief overview of the illustrated instrument, as shown in FIG. 2, the handle portion 102 is divided into two halves or shells 108 that, when joined, house or mount the various mechanical and hydraulic parts involved in clamping the effector jaws together and firing the staples. In brief, each handle shell 108 includes a fixed grip area 110, a body portion 112 and a distal spherical portion 114 that cooperates with other parts to provide a swivel or gimbal action between the handle assembly and the barrel assembly 106, as will be described in more detail later. The handle may be made of any suitable material such as rigid, injection molded plastic or the like.

The barrel portion 106 comprises a hollow elongated cylindrical barrel 116 may be made of suitable metal, although rigid plastic may also be used. The barrel is sufficiently small to allow introduction of the instrument through the lumen of a trocar or other introductory device employed in the surgical procedure for access through the skin of the patient to the surgical site. The barrel 116 contains the fluid flow tubing 118 and 120 of the hydraulic actuation systems for, respectively, closing the distal effector jaws and firing staples. In addition, the barrel contains a balloon retractor subassembly, generally at 122 in FIG. 2, that positively returns an actuator balloon to its retracted position after staple firing, as also will be discussed in more detail later.

The effector or implement end 104 of the instrument may be seen in FIGS. 1 and 3. In the illustrated embodiment, the effector end or implement is in the form of a pair of jaws for clamping and stapling tissue. The effector end includes a lower jaw 124 and an upper jaw 126 pivotally attached to the lower jaw. The lower jaw contains a prefilled staple cartridge that are ejected by hydraulic action. The upper jaw includes the anvil, which includes a series of curved convex surfaces for forming the staple ends over to clench the tissue gripped between the jaws. Of course, the jaw positions may be reversed and other end effector arrangements may be employed without departing from the present invention. For example, the jaws may include multiple rows of staples with a cutting element located between the rows to separate tissue upon stapling. The end effector could also include electrodes for radio frequency sealing, or could comprise scissor blades for cutting tissue. These are just a few of the additional possible applications of the instrument of the present invention.

The end effector assembly of FIGS. 1 and 3 is mounted to the distal end of the barrel 116 at an articulation joint, generally at 126, which allows relative side to side pivoting of the end effector jaws after they protrude through the distal end of the introduction trocar. In the illustrated embodiment, the end effector is spring-biased at the articulation joint to extend proximately 30 degrees in the direction out of the plane of the paper in FIG. 1. This feature of the illustrated instrument places the jaws in a preferred position for clamping and sealing the left atrial appendage of a human heart after entry between the ribs, in the procedure described in U.S. Pat. No. 5,306,234 to Dr. Johnson.

The Handle Assembly

Turning now to FIG. 2, as pointed out earlier, the jaw clamping and staple firing are hydraulically controlled, and each is controlled by a separate hydraulic system. The handle portion or assembly 102 mounts a hydraulic cylinder block 130 that includes a pair of parallel bores 132 and 134 for receiving, respectively, a piston for jaw clamping 136 and a piston for staple firing 138. The proximal end of each piston includes a gear rack for rack and pinion type cooperation with the gear teeth of separate clamping and for firing members. Coil springs 140 and 142 bias each piston toward a proximal, low pressure position.

It is contemplated that the hydraulic fluid used in these systems will be water or a combination of water-alcohol mixture to prevent the growth of organisms within the hydraulic fluid. Incompressible liquids are the preferred hydraulic fluid, but other liquids, and possibly even gases, could also be used as the hydraulic fluid, if so desired.

The clamping piston is moved forward, in a distal direction, by pivoting of clamp lever 144 toward the fixed pistol grip 110. Clamp lever 144 is pivotally mounted on cylindrical boss 146 that extends from the inside surface of handle shell 108. The clamp lever includes a raised arcuate segment that carries a series of gear teeth 148 on its upper surface, which engage with the teeth of the clamping piston gear rack 136, forming a rack and pinion arrangement. Upon pivoting of the clamping lever rearwardly, the clamping piston is forced forward or distally into bore 132, pressurizing the liquid located within the closed hydraulic system for the clamping action.

Figure 10:
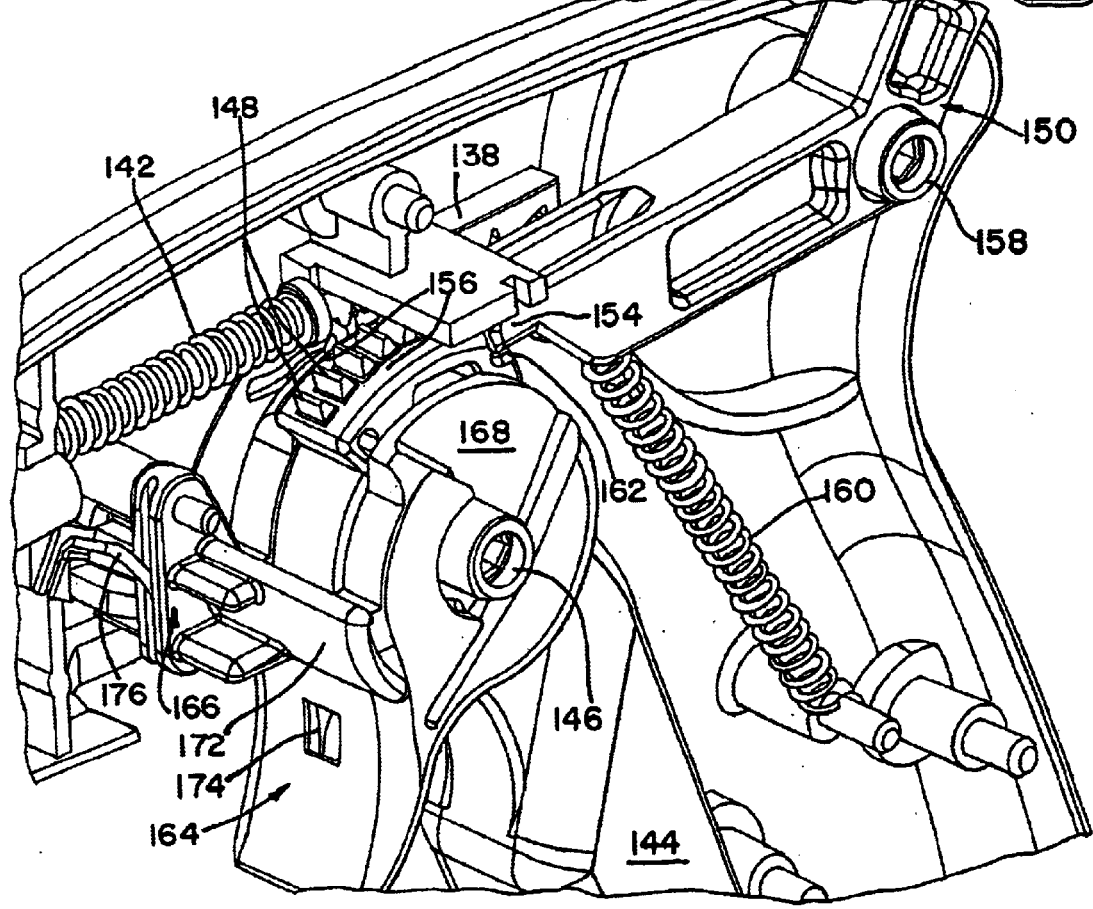
FIG. 10 is an enlarged perspective view of the handle assembly of FIG. 1 in a fully clamped position and with portions removed to better show the relationship between the clamping lever and firing trigger.
Figure 12:
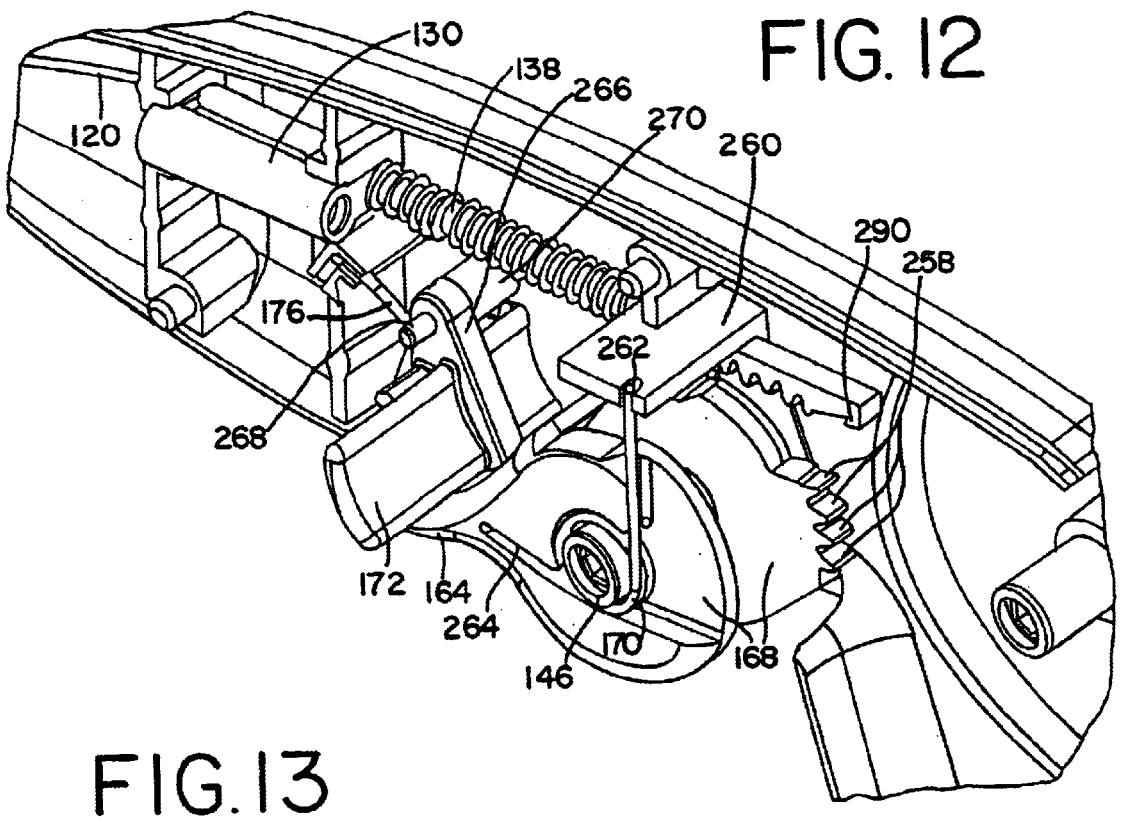
FIG. 12 is a perspective view of the handle of FIG. 11, taken from a different angle, showing the safety latch and the firing trigger in the undeployed, retracted position.

To lock the clamp lever in the clamped position, the handle assembly includes a release button 150. The release button has a proximal external thumb release tab 152 and a distal nose 154 that cooperates with upper surfaces 156 of the clamp lever that flank the gear teeth 148. The release button 150 is pivotally mounted on a cylindrical boss 158 (extending from the inside surface of housing shell 108) intermediate the thumb tab and the nose piece so that downward pressure on the thumb tab raises the nose piece. Coil spring 160 is attached to the release button to bias the nose downwardly. As will be described in more detail later, when the clamp lever is pulled to the clamping position, the nose of release button 150 falls into a locking notch 162 in the clamp lever to hold it in the clamped position. After the jaws are clamped, the next action required of the surgeon is to fire the staples so that they extend through and clench the tissue that is gripped between the closed jaws. To carry out this action, the handle assembly includes a firing trigger 164 and a safety latch 166. The firing trigger is also pivotally mounted on boss 146 of the handle. As can be seen in FIGS. 2, 12 and 10, in that order, the firing trigger has a pair of spaced-apart side walls 168. The upper end of the clamping lever is located within the space or slot between the side walls of the firing trigger, and the boss 146 extends through both the firing trigger and clamping lever.

The firing trigger is biased by torsion spring 170 to an extended firing position. However, until firing is needed, the trigger is held in retracted position within the handle by the safety latch 166. The safety latch 166 includes laterally extending wings 172 that extend through access openings or windows 174 in each side of the handle body 112.

The safety latch is also pivotally mounted to the body and biased by a spring wire 176 to a latched position, where it retains the firing trigger in an inaccessible retracted position within the handle until the surgeon wishes to fire the staples. At that time, the firing trigger is deployed by pushing on the end of one of the wings 172 that extends through side window in the handle. This action pivots the safety latch to a release position, allowing the firing trigger to deploy downwardly, due to the bias of torsion spring 170. The surgeon may then squeeze the firing trigger, causing gear teeth 258 on the upper surface of the firing trigger to move the staple firing piston forward, pressurizing the hydraulic fluid within the staple firing hydraulic circuit. The details of the various clamping and staple firing actions is shown more clearly in later drawings, where extraneous parts or pieces have been removed to clarify an understanding of the different operations of the illustrated device.

The Effector Assembly

Turning now to the distal or effector end of the instrument 100, the parts of the distal end may first be seen in FIG. 3, an exploded view.

The lower jaw 124 includes a bent u-shaped sheet metal channel 180 that includes an inclined slot 182 in each side wall and a pivot opening 184 in each side wall, where the upper jaw is pivotally attached to the lower jaw. The proximal end of the channel 180 is also formed into an articulation joint or knuckle, generally at 128, for pivotally joining, via pivot pin 129, with the distal end of the barrel or shaft 116.

The lower jaw includes a replaceable staple supply cartridge, generally at 186, which fits into a unshaped bent metal receiver 188 located within channel 180. The staple cartridge includes a side recess 189 for receiving a locator tab on the upper jaw where the jaws are clamped together. The lower jaw also includes a balloon housing 190 for housing the staple actuation balloon 192. The balloon terminates in a rounded balloon tip 194 for engaging against a wedge 196 in the staple cartridge. Axial expansion of the balloon forces the wedge through the staple cartridge, the sloped forward surface of wedge 196 forcing the staples upwardly out of the cartridge.

The upper jaw 126 of the end effector includes an anvil body 198 that has pivot openings 200 for pivotal attachment to the lower jaw pivot openings 184 by pivot pin 202. The anvil body 198 also includes a pair of slots 204 that cooperate with inclined slots 182 in the lower jaw, via slide pin 206, for relative opening and closing of the jaws. The anvil body further includes a staple cartridge locator tab 207, for insertion into the side recess 189 of the staple cartridge for positively locating the staple cartridge when the jaws close.

The upper jaw 126 also includes a nose piece 208 that has a central bore 210 for receiving piston 212. The piston 212 cooperates with a linkage 214 to open and close the jaws. More specifically, piston rod 216 extends through linkage eye 218 and through a coil spring 220 and into the nose piece bore 210 (with bushing 211 closing the proximal end of the nose piece bore except for a small hydraulic fluid port in the bushing). The linkage 214 includes pivot openings 222 that cooperate, via slide pin 206, with the slots 204 in the anvil body and inclined slots 182 in the lower jaw channel, as will be described in more detail later. Finally, the upper jaw includes an anvil former 224 which has concave pockets for receiving and bending over the staples to clench tissue gripped between the jaws, and a torsion spring 226 for laterally biasing the jaws to a angle position relative to the barrel 116.

The Barrel Assembly

Referring to FIG. 2, the barrel or shaft assembly 106 includes the barrel or shaft 116 which houses the hydraulic tubing 118 and 120 for the closing and firing systems and the balloon retractor subassembly 122. As mentioned earlier, the barrel or shaft 116 is a hollow, cylindrical, elongated tube, and is preferably made of metal, although suitably strong plastic may also be used. The proximal end of the barrel 116 includes opposed slots 228 for attachment to swivel joint 298 between the handle and barrel. The distal end of the barrel has upper and lower pivot openings 232 for receiving pivot pin 129 that joins the barrel and jaws to form the articulation joint 128.

The balloon retraction subassembly 122 located within the barrel includes a balloon retractor tube 234 extending longitudinally within the barrel and closed at each end by a bushing 236. Hydraulic fluid from the staple firing piston communicates with the interior of the balloon retractor tube through tubing 120 that is attached to a hydraulic fluid port in the proximal bushing 236. The hydraulic fluid path extends through the distal end bushing 236 to an extension of tubing 120 that continues to the proximal end of balloon 192, located in the lower jaw of the effector assembly.

The balloon retractor tube 234 encloses, as best seen in FIGS. 26–28, a cable cap 238 attached to the proximal end of a retractor wire 240. Retractor wire 240 extends through the distal bushing 236, through the extension of tubing 120 and through the balloon to the balloon tip 194. Coil spring 242 extending between the distal bushing of the retractor tube and the cable cap 238 biases the end cap to a proximal position, which corresponds to a balloon retracted position. With this arrangement, expansion of the balloon pulls, via wire 240, cable cap 238 in a distal direction, compressing coil spring 242. When the hydraulic force is reduced after staple firing, the force of the compressed coil spring pushes the cable cap rearwardly (proximally), pulling the wire 240 and thus the balloon to a retracted or deflated position.

The Clamping Action

FIGS. 4–9 show cross-sectional views of the handle portion and end effector portion with respect to the clamping operation, with parts and pieces relating to the firing action removed for better understanding of the clamping action.

Figure 4:
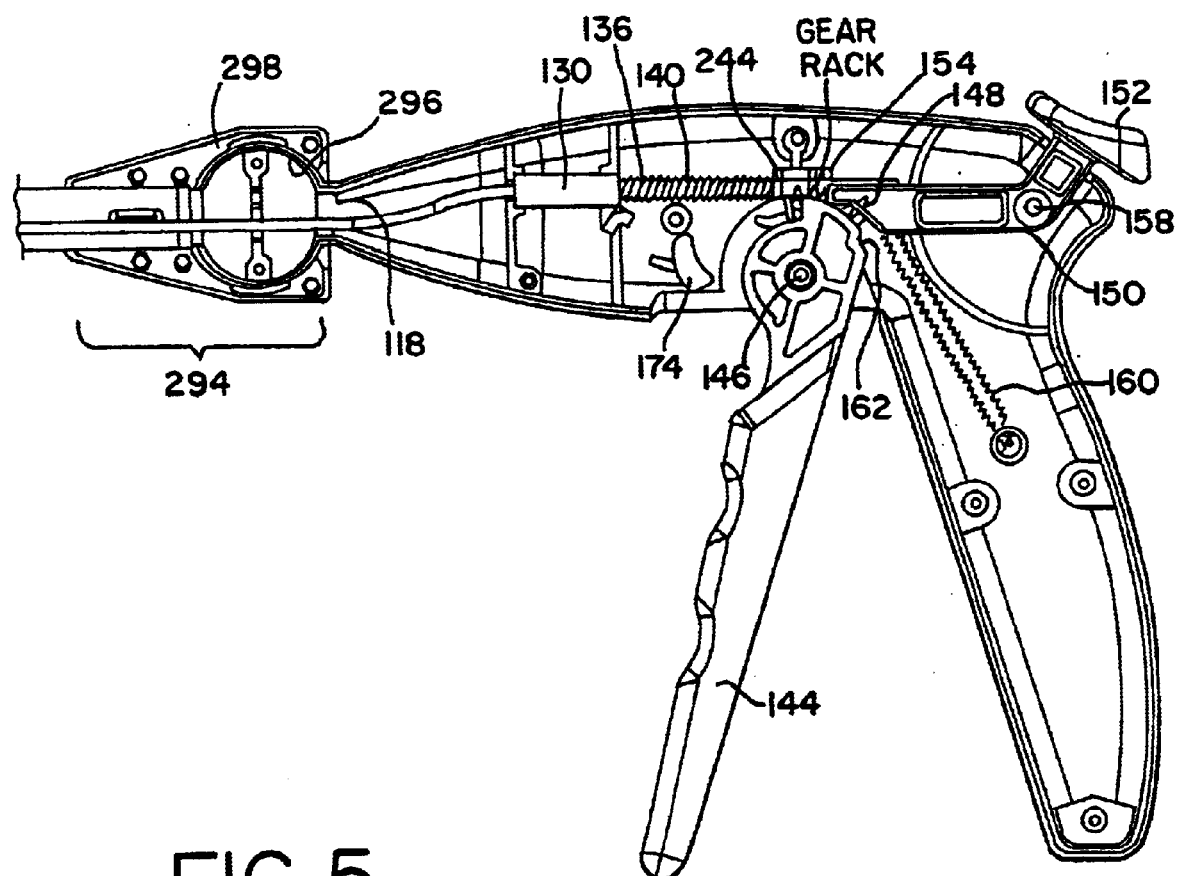
FIG. 4 is a vertical cross-sectional view of the handle assembly and articulation joint between the handle and barrel of the instrument of FIG. 1, with the jaws in the fully open position, and with portions pertaining to the staple operation removed for better illustration of the clamping operation.
Figure 5:
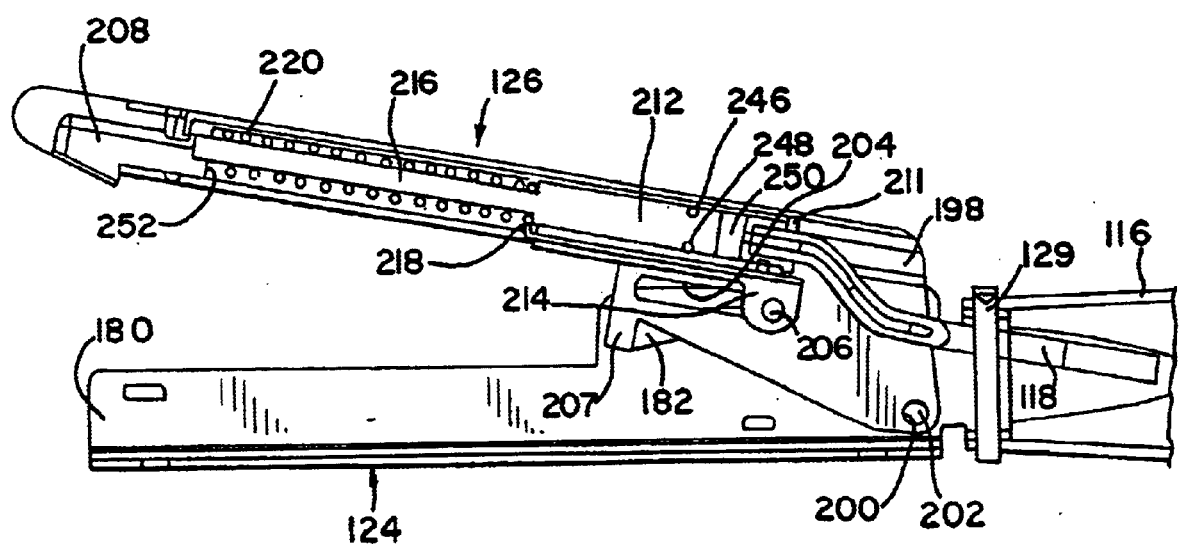
FIG. 5 is an enlarged vertical cross-sectional view of the end effector portion of the instrument of FIG. 4, with the jaws fully open, and with portions relating to stapling removed for better understanding of the clamping operation.

FIGS. 4–5 show the handle assembly and effector assembly as they are in the jaws open position. Turning to FIG. 4, the handle assembly 102 is shown there in cross-sectional view, illustrating the clamp lever 144 pivotally mounted on boss 146, the hydraulic cylinder block 130, and the clamping piston 136 which includes a gear rack at its proximal end. Flexible tubing 118, which may be plastic, silicone or other suitable material, extends from the clamping piston bore 132 to the distal end jaws for effecting the clamping action. The tubing is flexible at least in the vicinity of or in proximity to the articulation joints so as not to substantially interfere with or impair articulation of the joint. Compressed coil spring 140 extends between the hydraulic cylinder block 130 and flange 244 located on the piston. Coil spring 140 biases piston toward a proximal, low pressure position, so as to bias the effector jaws in an open position.

In the position illustrated in FIGS. 4–5, the jaws are fully open, the clamp lever 144 is fully extended, and the clamping actuation piston is in the position fully to the right in the non-pressurized proximal position. The distal nose 154 of the release button 150 rests on the smooth upper surfaces 156 of the clamp lever 144 (See FIG. 10). Coil spring 160 is in tension, pulling the nose of the release button downwardly. As better seen in FIGS. 1 and 10, the distal or nose end of the release button is slotted. The clamping piston gear rack is slidably received within the nose piece slot, and the nose piece therefore prevents lateral, side-to-side shifting of the piston gear rack.

Turning to FIG. 5, showing the end effector jaws in the open position, comparable to FIG. 4, the effector jaws are shown in cross-sectional view, without a staple cartridge, to better illustrate the clamping function. As shown there, the anvil body 198 is pivotally mounted by pivot pin 202, which extends through pivot openings 184 of the lower jaw channel and 200 in the upper jaw anvil body. Slide pin 206 extends through slots 182 in the lower jaw channel, slots 204 in the upper jaw anvil body, and through pivot openings 222 of the linkage 214. Piston 212 is located within the bore 210 of the nose piece 208. The piston includes an o-ring 246 located in an o-ring slot 248 around the circumference of the piston to seal against the leakage of hydraulic fluid.

The proximal end of the nose piece is closed by a bushing 211, to which the hydraulic tubing 118 is attached. The fluid space 250 located between bushing 211 and piston 212, in normal operation, will be filled with hydraulic fluid. Upon pressurization of the hydraulic fluid, the piston will be moved distally or forwardly (to the left in FIG. 5). As will be recalled, the piston rod 216 extends through the eye 218 of the linkage 214, and movement of the piston to the left also pushes the linkage to the left.

The forward or distal end of the nose piece is slotted on the underside to receive the eye 218 of linkage 214. As the piston moves to the left, action of the slide pin 206 moving along slots 204 in the upper jaw anvil body and 182 in the lower jaw channel pull the slots together, closing the jaws. Movement of the piston also compresses the coil spring 220 that extends between an inner shoulder 252 on the nose piece and the linkage eye 218. Accordingly, in the event of failure of the hydraulic clamping system, the spring 220 will move the piston 212 to a jaw-open position.

Figure 6:
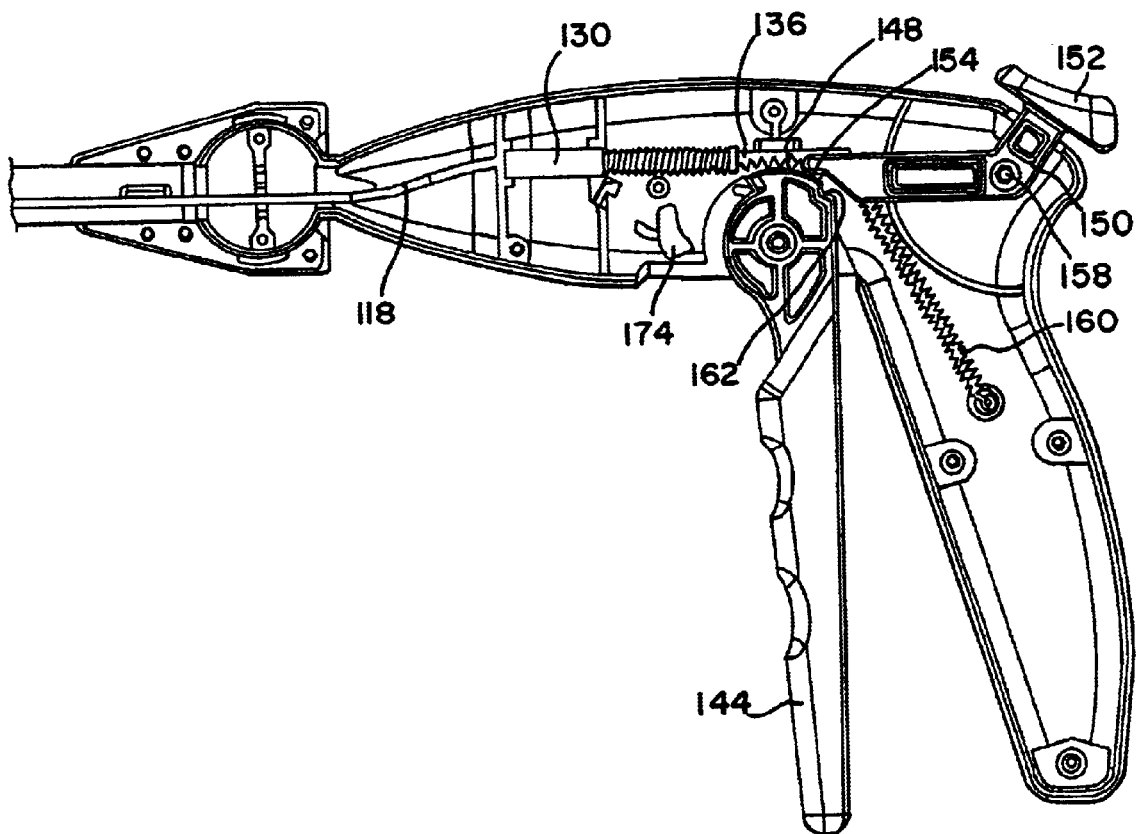
FIG. 6 is a vertical cross-sectional view of the handle assembly of FIG. 4, but with the jaws at an intermediate position.
Figure 7:
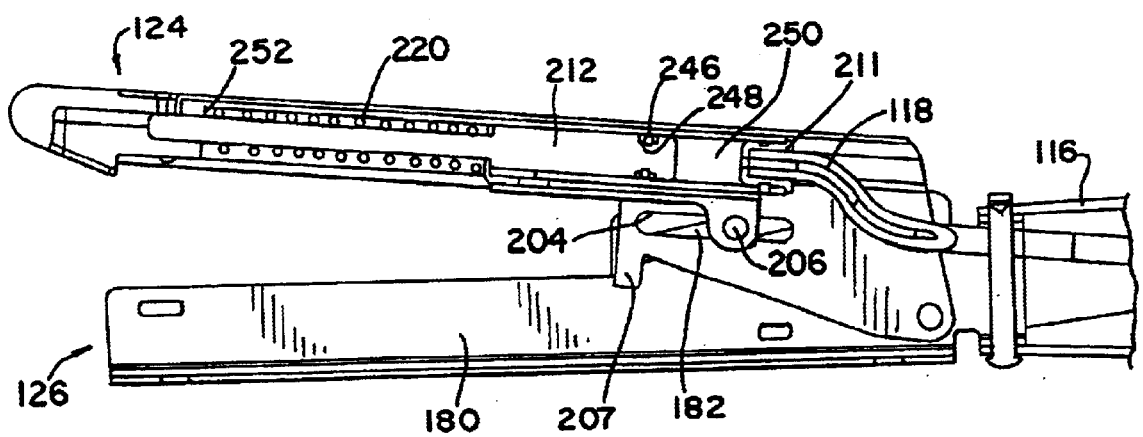
FIG. 7 is an enlarged vertical cross-sectional view of the end effector portion of FIG. 5, but with the jaws at an intermediate position.

FIGS. 6 and 7 show the handle assembly 102 and end effector assembly 104 in the position where the jaws are partially closed. As can be seen in FIG. 6, the clamp lever 144 has moved partially toward the fixed pistol grip 110. The rack and pinion gear arrangement between the clamping piston 136 and clamp lever gear teeth 148 has moved the clamping piston slightly distally or to the left in FIG. 6, pressurizing the hydraulic fluid within the bore 132 of the hydraulic cylinder block 130. Inasmuch as this is a closed hydraulic system full of normally incompressible liquid, little movement is required to generate very high pressures within the hydraulic system. This increased pressure is transmitted through the tubing 118 to the piston 212 located in the upper jaw at the distal end of the instrument.

Turning to FIG. 7, increased hydraulic pressure through the tubing 118 and bushing 211 has moved the piston 212 slightly in the distal direction (to the left in the drawing) pulling the linkage 214 in a distal direction, and moving slide pin 206 distally along slots 204 in the upper jaw anvil body and 182 in the lower jaw channel. This action of the linkage and pin has drawn the upper and lower jaws of the distal end together.

Figure 8:
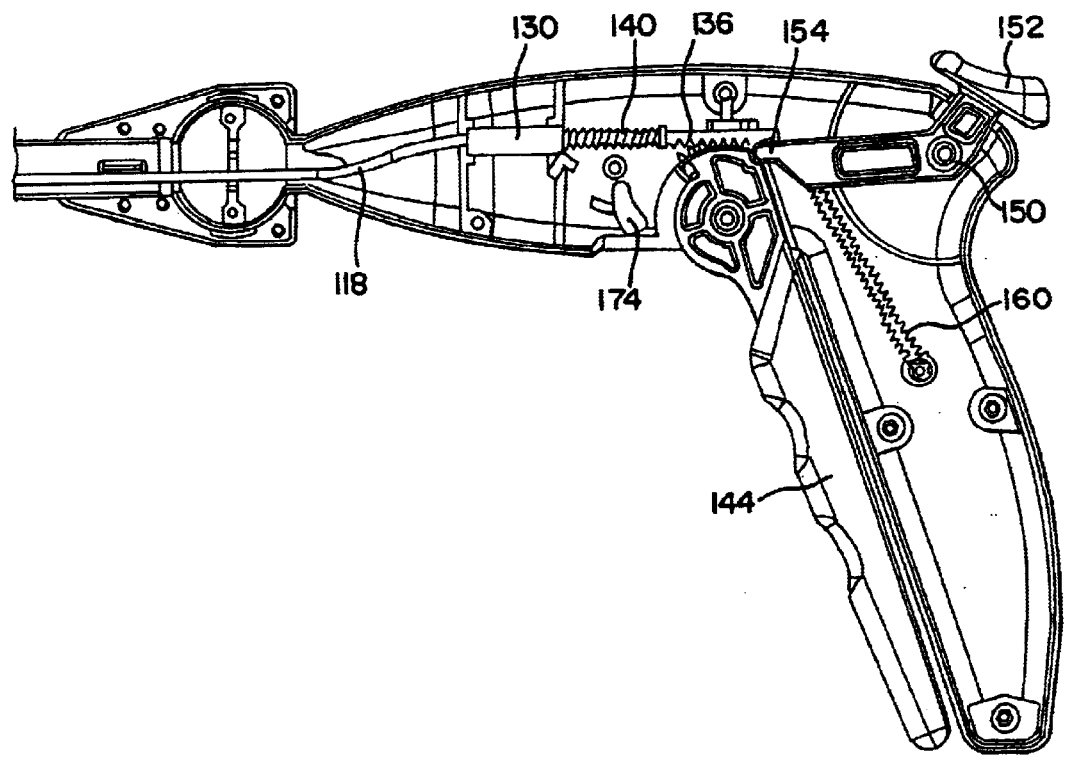
FIG. 8 is a vertical cross-sectional view of the handle assembly of FIG. 4, but with the jaws at a fully closed position.
Figure 9:
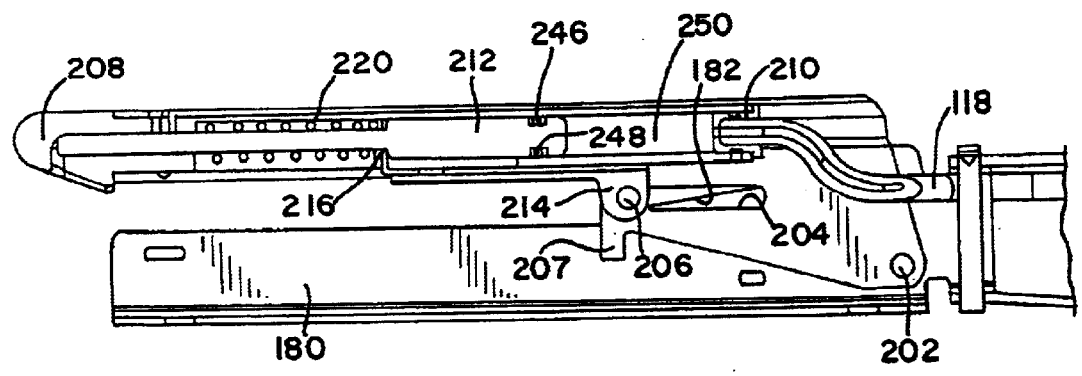
FIG. 9 is an enlarged vertical cross-sectional view of the end effector portion of the instrument of FIG. 5, but with the jaws at a fully closed position.

FIGS. 8 and 9 show the instrument 100 with the jaws 124 and 126 fully closed or clamped. As seen in FIG. 8, the clamp lever 144 has now been pivoted fully against the pistol grip 110. Nose end 154 of the release button 150 has dropped into the locking notch 162 in the upper area of the clamp lever, preventing the clamp lever from rotating clockwise, unless the thumb release tab 152 is depressed. Coil spring 160, which is in tension, holds the release button in this locked position.

In the fully clamped position, the gear teeth 140 on the upper end of the clamp lever 144 have advanced the clamping piston 136 more completely in the compressed direction (to the left in the drawing), creating increased pressure in the clamping hydraulic circuit and further compressing piston coil spring 140.

As shown in FIG. 9, the increased pressure of the hydraulic liquid, communicated through the tubing 118 and into the bore of the nose piece 208 has moved the piston 212 in upper jaw 126 distally. As a result, the piston 212 has pushed the linkage 214 toward the distal end of the jaw and the slide pin 206 to the distal end of the slots 204 in the upper jaw anvil body and 182 in the lower jaw channel. This action brings the jaws to the fully closed or clamping position. Again, coil spring 220 is compressed, biasing the piston to the low pressure or jaws open position.

When it is desired to open the jaws, the above described action is reversed. The thumb tab 152 on the release button 150 is depressed, raising the nose 154 of the release button from the lock-out notch 162 in the clamp lever, and allowing the clamp lever to rotate clockwise to the open position. The bias of the compressed springs 220 in the upper jaw and 140 in the handle force the clamping piston 136 outwardly of the bore 130 in the hydraulic cylinder block to a low pressure position, where it was initially, as seen in FIG. 4 for example, and the jaws open by the reverse movement of slide pin 206 in the slots 204 in the upper jaw anvil and 182 in the lower jaw channel.

The Stapling Action

Turning now to the stapling action, the hydraulic circuit of the stapling action may be seen in FIGS. 12–26. As was pointed out earlier, the hydraulic system for the firing circuit has, at the proximal end, the staple firing piston 138, which is slidably received within bore 134 of the hydraulic cylinder block 130. As with the clamping hydraulic circuit, the firing hydraulic circuit is a closed circuit, pre-filled with essentially non-compressible liquid, although other fluid and even compressible gas may be employed if desired. Hydraulic fluid is conducted through flexible tubing 120, balloon retractor tube 234, tubing 120 extension and into the balloon 192, so that the tubing is located in proximity to the joints to allow articulation without substantial interference and without complicated mechanical structures for transmitting control actions to the end effector. Both clamping and firing pistons include one or more o-rings to seal against the respective bore to prevent leakage of hydraulic fluid.

Figure 11:
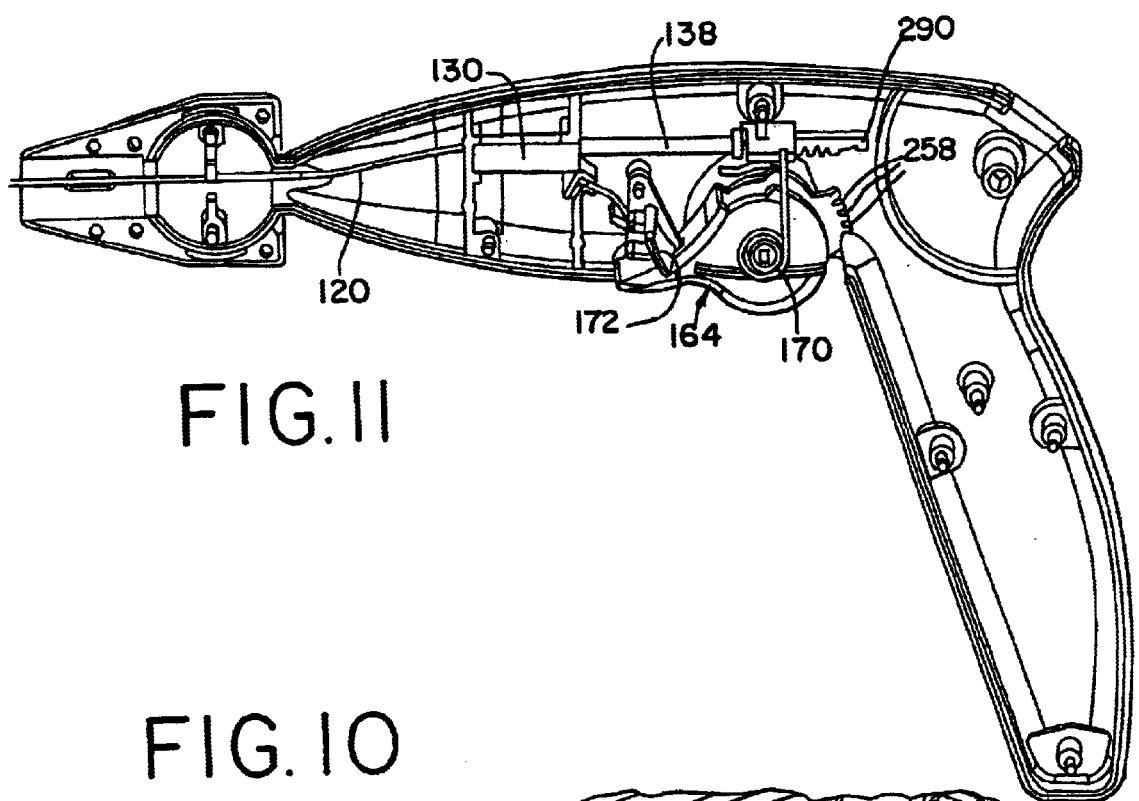
FIG. 11 is a perspective view of the handle of the instrument of FIG. 1, with portions removed to better illustrate the firing trigger and safety latch, and with the firing trigger in the undeployed position.
Figure 13:
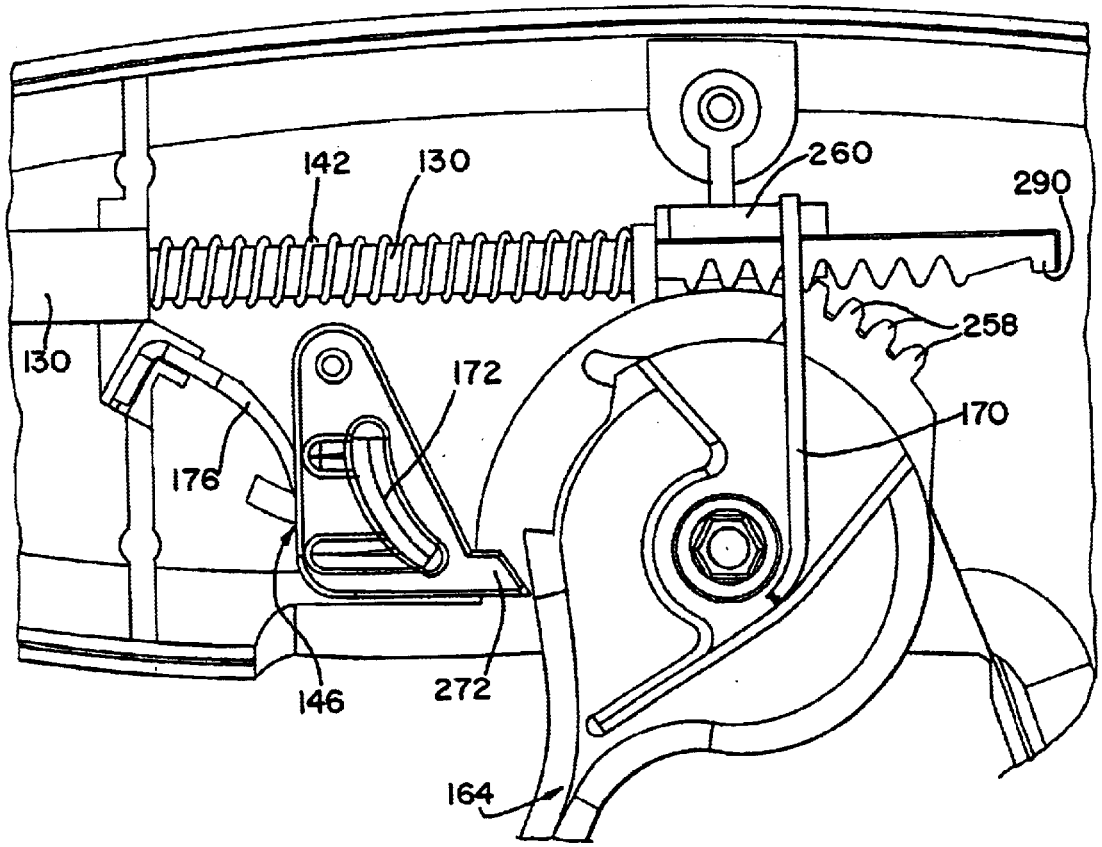
FIG. 13 is an enlarged side view of the handle of FIG. 11, and of the firing trigger and safety latch in particular, with the firing trigger in the deployed position.
Figure 14:
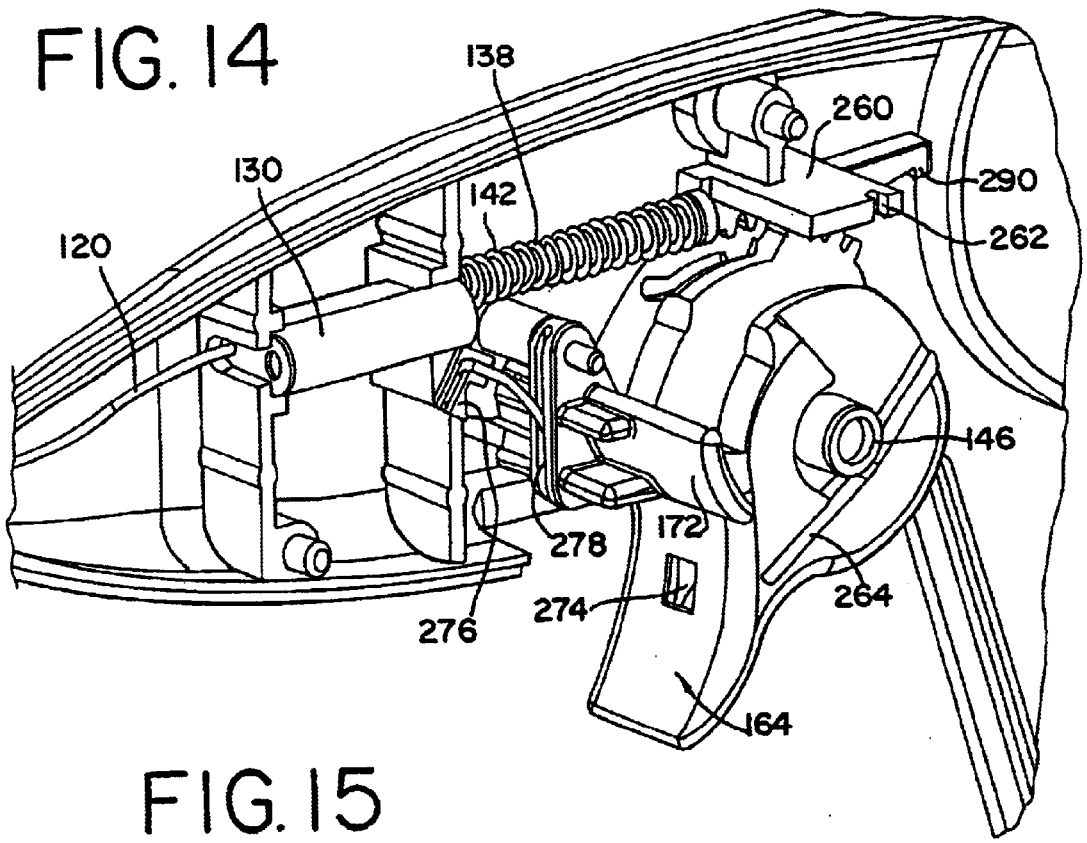
FIG. 14 is a perspective view of the handle of FIG. 11, taken from a different angle to better illustrate various aspects of the firing trigger and safety latch.
Figure 15:
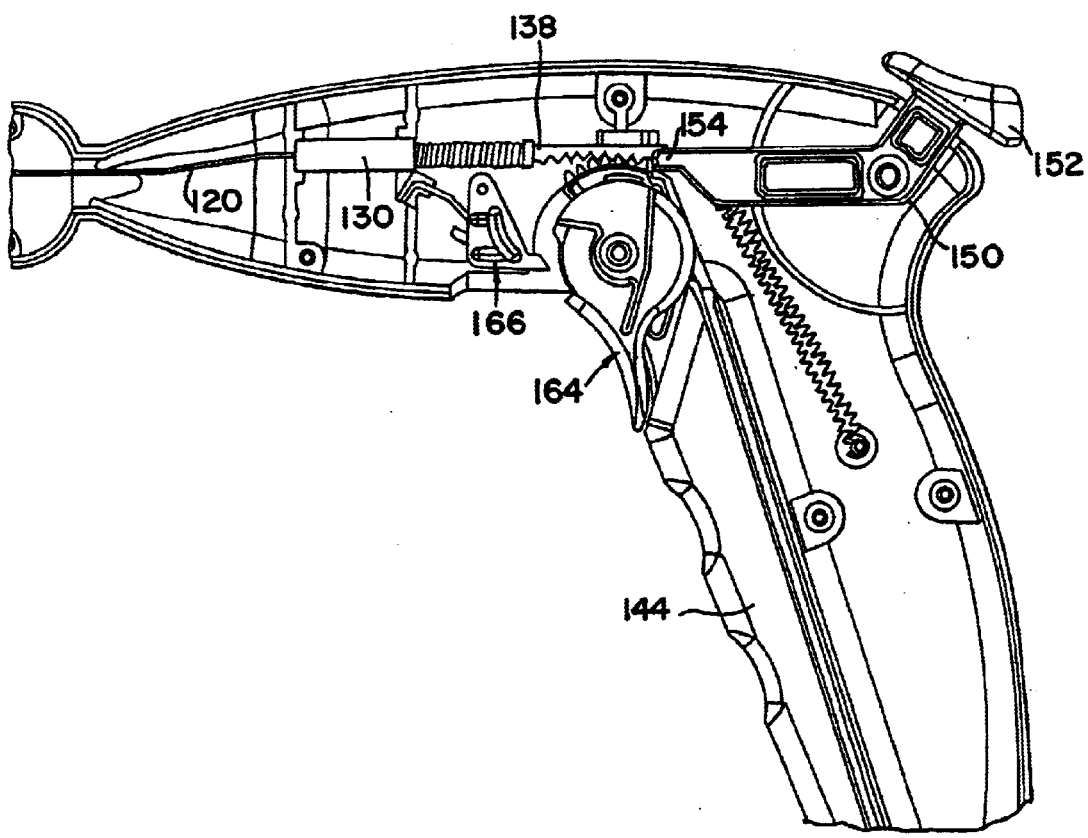
FIG. 15 is a side view of the handle of the instrument of FIG. 1, with parts removed to illustrate the firing trigger and safety latch, with the firing trigger in the fired position.

The handle mechanism by which the staple firing sequence occurs is perhaps best seen in FIGS. 11–15, which are views of the inside of the handle, with parts relating to the clamping action removed. Turning first to FIG. 11, the firing trigger 164 is shown in the retracted and undeployed position, where it is held by the safety latch 166 until the surgeon takes the positive step, after being satisfied with the clamping, to deploy the firing trigger. As may be seen in FIG. 12, the firing trigger is pivotally mounted on the same boss 146 as the clamp lever 144. More specifically, the firing trigger includes a pair of spaced apart circular side or end walls 168, one of which includes gear teeth 258 for cooperation with the gear rack of the staple-firing piston 138, and the other of which mounts the torsion spring 170, which biases the trigger to the deployed position. In the completed assembly (See FIG. 10), the upper end of the clamp lever 144 is located and captured between the spaced-apart circular walls 168 of the firing trigger, rotating freely relative to the firing trigger on the boss 146. As shown in FIG. 14, the rack of the staple firing piston is constrained against upward movement by a horizontal plate 260. The horizontal plate also includes an aperture 262 for receiving one arm of the torsion spring 170. The other arm of the torsion spring is captured in a slot 264 provided in the side face of the firing trigger.

To hold the firing trigger in a retracted and inaccessible position until after the surgeon is satisfied with the clamping, the present invention employs the safety latch 166. As seen in FIGS. 1 and 12, the safety latch 166 includes a vertical wall or body 266 which mounts, at its upper end, opposed pivots 268 that extend into hollow bosses 270 of the handle, allowing the safety latch to pivot or swing about those pivot points. As seen in FIG. 13, a tongue or tab 272 protrudes proximally from the face of the safety latch for engagement with a window 274 (as best seen in FIG. 14) in the safety latch trigger. One end of spring wire 176 is attached, as seen in FIG. 14, to partition 276 of the handle. The other end of the spring wire is located in a slot 278 in the back side of the safety latch body 266. Thus, the spring wire biases the safety latch counterclockwise, so that the tongue 272 enters the trigger window 274 when the trigger is moved to a retracted position.

As described briefly earlier, the safety latch includes a pair of wings 172 extending laterally from the body 266, and through windows 174 in the side walls of the handle. When the surgeon is satisfied with the clamping action, he or she may, by pushing on the end of the wings protruding through the window, pivot the safety latch clockwise to remove the latch tongue 272 from the firing trigger window 274, and allow the firing trigger to deploy under the biasing force of the torsion spring 170.

In the deployed position, the firing trigger is accessible to the surgeon for executing the firing action of the staples. Similar to the clamping action, pulling on the trigger causes, through the meshing of gear teeth 258 and the teeth of the staple firing piston rack, the staple firing piston to move distally to compress the hydraulic fluid in the firing piston bore 134 and to compress the coil spring 142 that surrounds the firing piston. As hydraulic pressure is increased by the movement of the piston in the handle, the increased pressure is transmitted to the balloon 192 through the hollow tube 120, the balloon retractor tube 234, and tubing extension.

The staple firing sequence in the distal lower jaw is most easily understood by reference to FIGS. 18–25. FIG. 18 is a perspective view of the end effector, which shows both the top and bottom jaws 124 and 126 of the preferred embodiment of the present invention. In FIG. 19, the upper jaw is removed, and only the lower jaw with the staple cartridge 186 remains. In that figure, the inclined slots 182 in the channel 180 are readily visible, as is the pivot opening 184 by which the upper jaw is pivotally attached to the lower jaw. The articulation joint 128 and pivot pin 129 mounting the end effector to the distal end of the barrel are also visible in FIG. 19.

In FIG. 20, the channel is removed, and we can now see the receiver 188, containing the staple cartridge 186, and also the balloon housing 190. A balloon housing tab 280 is located on each side of the balloon housing 190 for snap interfit in side apertures 284 in channel 180 (see FIG. 19).

FIG. 21 shows the distal end of the lower jaw with the receiver and staple cartridge, in large part, removed. In this figure, tubing 120, which conveys the hydraulic fluid to the balloon, is shown entering the rear or proximal end of the balloon housing 190. The rear of the balloon housing also includes an arcuate or cutout area for accommodating the pivot pin 202 that pivotally mounts the lower and upper jaws together. The balloon housing 190 has a generally U-shaped cross-sectional shape, forming a channel for receiving the deflated or retracted balloon. The convex, hemispherically shaped tip 194 of the balloon may be seen at the distal end of the housing in FIG. 21. FIG. 21 also shows the cam or wedge 196 which, when forced axially through the staple cartridge, ejects the staples. The proximal end of the wedge is generally spherically concave in shape to receive the spherically convex tip of the balloon. The wedge also includes a ramp or cam surface 284.

Within the staple cartridge, as is well known in the prior art, each staple 286 is located atop a driver 288, and the drivers are aligned in a generally axial direction. As the wedge is forced forward or distally through the cartridge, the drivers are forced up the ramp surface of the wedge, ejecting the staples and forcing them against the anvil former that is located in the upper jaw.

The balloon 192 has a fluted wall which allows it to be repeatedly expanded and retracted. As shown in FIG. 22, the balloon is in the retracted position. When the firing trigger is pulled, and the staple firing piston increases hydraulic pressure in the firing circuit, the balloon expands axially, as shown in FIG. 23, forcing the wedge through the cartridge and firing the staples into and through the tissue and forming the ends of the staples over to clench the tissue gripped there between.

FIGS. 37 and 38 shows a vertical side cross-sectional view of the balloon when expanded and retracted, and showing the fluted or folded accordion configuration of the balloon.

Figure 16:
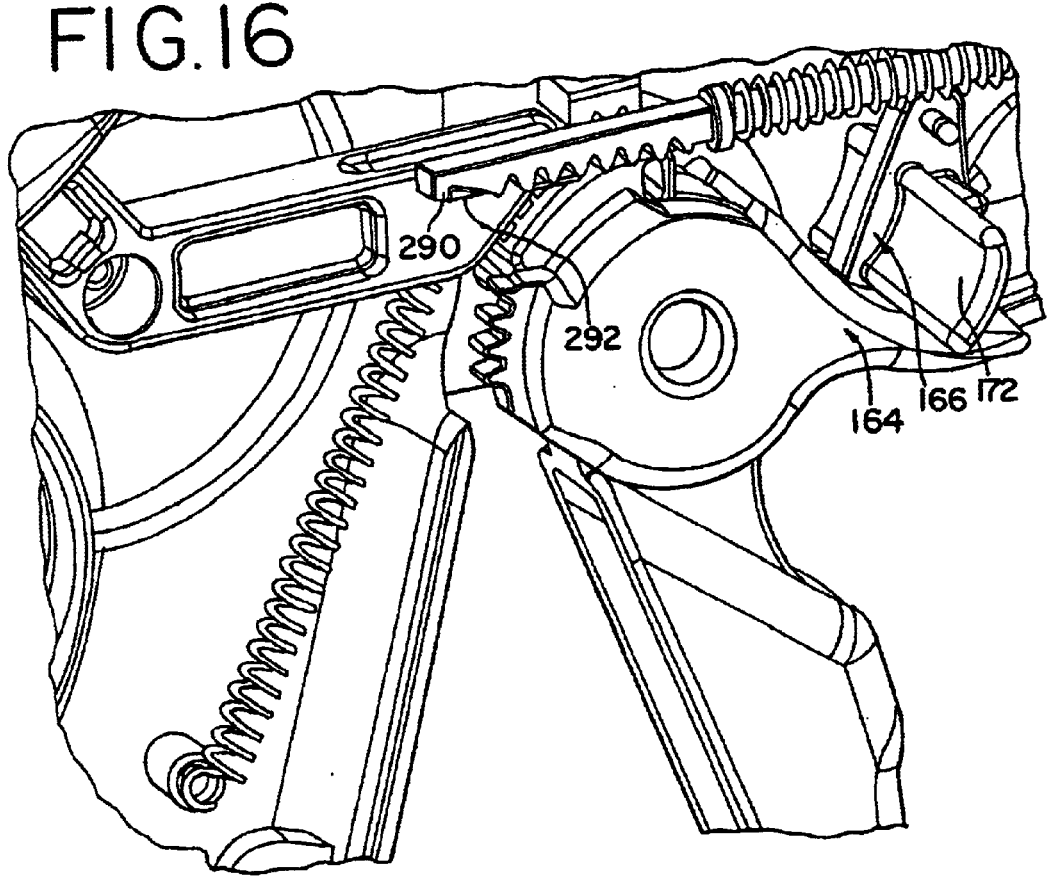
FIG. 16 is an enlarged perspective view of a portion of the handle assembly of the instrument of FIG. 1, taken from the back side of the instrument as depicted in FIG. 1 and illustrating, among other things, a firing lockout feature that prevents staple firing until the instrument is fully clamped.
Figure 17:
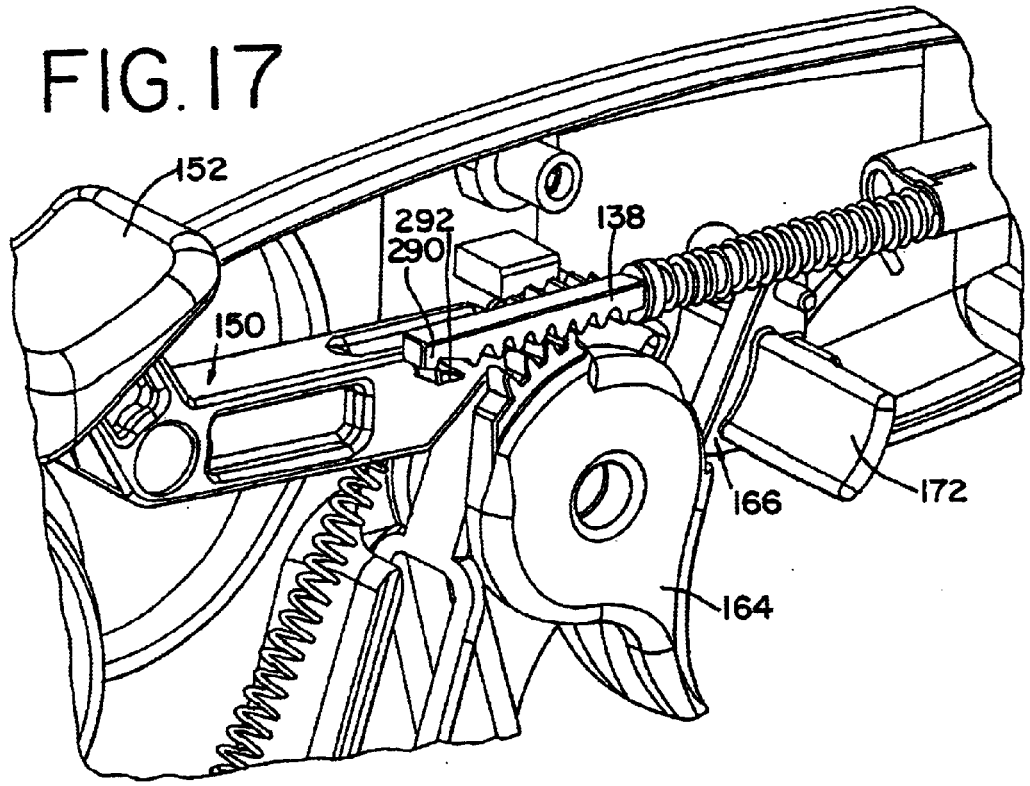
FIG. 17 is a view comparable to FIG. 16, but showing the trigger lockout in a released position.

There is yet one additional safety feature associated with the firing of the staples in the instrument 100. Turning to FIG. 16, a depending hook 290 is located at the proximal end of the staple firing piston 138. That hook is engaged by a raised tab 292 on the nose 154 of the release button 150 until the jaws are clamped. This interference prevents axial movement of the staple firing piston until after the jaws have been fully clamped. It may be recalled from FIG. 8, that after the clamping lever is fully retracted, the nose of the release button falls into the locking notch 162 in the upper surface of the clamp lever 144. When that occurs, the raised tab on the release button drops out of engagement with the staple firing piston (see FIG. 17), allowing the piston to be moved by the firing trigger. Until such time, however, as the release button drops into the notch in the clamp lever, which occurs only in the fully clamped position, inadvertent or accidental firing of the staples is prevented.

Articulation Joints

As best seen in FIG. 4, a swivel or gimbal joint is shown in the nature of a ball and socket joint 294. As can be seen in FIG. 2, the distal end of each half of the handle includes a hemispherical portion 114, such that when the two handle halves are joined, a ball 296 is formed at the distal end of the handle portion.

Slidably mounted over the ball is a socket 298, also formed by joining two halves, which includes a distal bore 300 for fixedly receiving the proximal end of the barrel or shaft 116. The proximal inside surface of the socket is curved to match the hemispherical shape of the ball, forming a relatively tight but still slidable frictional fit between the ball and socket. For locking engagement of the proximal end of the shaft into the socket, each socket half includes a inwardly extending tab 302, which enters a mating slot 228 in the proximal end of the barrel. This serves to lock the barrel or shaft in a fixed position relative to the socket. Accordingly, with this construction, the handle may be pivoted relative to the barrel or shaft in any direction for up to about 20 degrees.

As clear from the description, the end effector of the present invention is also articulated relative to the barrel or shaft. As best seen in FIGS. 3 and 19, the proximal end of the lower jaw channel 180 is bent into a series of tabs 304, each of which includes a pivot opening 306 in axial alignment with the others. The distal end of the barrel, as also seen in FIG. 3, includes upper and lower axially aligned pivot openings 232. Pivot pin 129 extends through aligned pivot openings 232 in the distal end of the barrel and the aligned pivot openings 306 in the bent tabs of the lower jaw channel 180. This forms a hinged type of joint, allowing pivoting movement of the jaws laterally left and right relative to the barrel.

For particular application of this device to the isolation of the atrial appendage, torsion spring 226 is located on the vertical pin, biasing the jaws at a lateral angle of about 30 degrees relative to the barrel, although other degrees of biasing may be employed, if desired. The spring allows the jaws and barrel to be in alignment as they pass through the trocar in the patient and to the treatment site, but as the distal end of the instrument emerges from the trocar, the jaws move to the angled position to which it is predisposed by the torsion spring.

The end effector may also be mounted for articulation in other directions, such as vertically or at another angle. Also, the articulation joint between the barrel and end effector may be a gimbal or ball and socket type joint, such as used between the barrel and handle, for 360° of articulation. With such a joint, control wires extending from the handle, through the barrel and to the end effector could be used to control the direction and amount of articulation of the end effector to effect precise changes or adjustments to the position of the end effector, as may be required for particularly delicate medical procedures.

FIGS. 39*a–e* show an alternative embodiment of the present invention. As with the instrument described above, the version shown in FIGS. 39*a–e* includes a handle portion 102, end effector portion 104 and barrel portion 106. In this embodiment jaws 300 and 302 are pivotally attached at 304 for opening and closing in a scissor-like movement. In addition, each jaw has a terminal portion that is separately pivotable at 308 to allow pivoting of the terminal portion of the jaws at up to a right angle with respect to the barrel portion 106 (as shown in FIG. 39*a*). With this construction, the jaws may be in general alignment with the barrel for passage through a trocar, and then pivoted to any desired position at the surgical site.

Shaft Configuration

FIGS. 40–65 illustrate a further aspect of the present invention. The instrument preferably includes a shaft which is capable of an angled configuration where at least a portion of the shaft is manually movable to a direction which extends at an angle to another portion of the shaft. The angled shaft portion may be angled in one or more directions or planes. Each of the angled shaft configurations illustrated in FIGS. 40–65 is shown by way of example and not limitation. Numerous other configurations of the shaft are also possible without departing from this aspect of the present invention and may depend upon the medical procedures employed, the method of approach utilized in the medical procedure, as well as the area which is to be treated. It is realized that at least a portion of the shaft may be shaped by the operator prior to insertion of the instrument into the patient and/or after the instrument is inserted in the patient. Manual manipulation or shaping of the shaft may be performed directly or indirectly by the operator via control rods extending through the shaft to the handle portion, as will be described, so that the shaft is conformed into a desired configuration.

In FIGS. 40–42 an instrument, generally indicated at 400, similarly includes a handle portion 102 at the proximal end of the instrument, a distal end effector 104 and a shaft assembly 106. The shaft assembly 106 includes an outer flexible shaft 404 as best seen in FIGS. 41 and 42. At least one fluid flow path 406 is disposed preferably within the flexible outer shaft 404 though it is realized that any number of fluid flow paths may be utilized as previously described with another aspect of the present invention.

The flexible outer shaft 404 includes a proximal end, generally indicated at 408, and a distal end, generally indicated at 410. The elongated shaft defines a longitudinal shaft axis, generally indicated at 412, at the distal end thereof. At least a portion of the shaft may be manually moveable to a direction in which it extends at an angle to another portion of the shaft. For example, the shaft 106 may be shaped from the straight orientation as illustrated in FIG. 1 to the angled orientation which is illustrated in FIG. 40 and which shows a portion of the shaft such as the distal end portion 410 extending at an angle relative to the remaining portion of the shaft. It can be seen that in FIG. 40 the longitudinal access 412 on the shaft, therefore, does not lie in a straight orientation as compared to the shaft of FIG. 1. Rather, the shaft in FIG. 40 has a downwardly curved shaft portion in proximity to the handle portion and an upwardly curved shaft portion in proximity to the distal end effector. So, it can be seen that one or more portions of the shaft may be angled or deflected relative to another portion of the shaft. In addition, the angled shaft portion may be moved in one or more directions which are at an angle to another portion of the shaft. Although the angle of deflection is most likely an acute angle, other angles of deflection will be apparent. The angled shaft portion may be more sharply angled or more gradually angled so as to achieve a desired configuration.

The flexible outer shaft 404 is preferably made of a polymer which is flexible along its length or, alternately, may be made of a metallic material and/or other suitable materials as well as a combination of any of the aforementioned materials such as where the shaft has a multi-layered construction. It is contemplated that the polymeric material may be resilient, so that it tends to return to its original shape, may be capable of shape retention whereby the flexible outer shaft will remain in the configuration in which it is positioned, or may be made of a material which allows the shaft to be freely conforming to the pathway defined by the surrounding environment. Where the shaft is capable of shape retention, the shaft may be manually moveable by the operator such as prior to insertion of the instrument into a patient or directly or indirectly at any time thereafter. Where the shaft is resilient or freely conforming, movement of the shaft may effectuated by exterior surfaces such as, for example, trocars or insertion sleeves which have the desired angled configuration acting upon at least a portion of the shaft so as to manually move, bias, flex or bend the shaft along that portion.

FIGS. 43–46 illustrate another instrument 414 which similarly includes a handle portion 102, a distal end effector assembly, and a shaft assembly 106. The shaft assembly includes a flexible outer shaft 416 which generally defines a shaft axis 417. The shaft assembly further includes fluid flow paths 418 and a elongated malleable element 420. The shaft is preferably made of plastic although, as described above, other materials are also possible. In accordance with the previously described aspects of the present invention, the fluid flow paths 418 are used to effect selective actions of the hydraulic actuator.

In FIGS. 43–46 the malleable element 420 extends along the elongated shaft, preferably between a proximal end 422 and a distal end 424 of the shaft although it is possible that the malleable element may be disposed along a portion of the shaft and/or extend discontinuously along several portions of the shaft. Towards this end, numerous longitudinal lengths of the malleable element will be possible depending the configuration which is desired. The malleable element may be comprised of one or more members extending along all or a portion of the shaft. The malleable element is preferably made of metallic material such as a metal rod, wire or the like which is capable of shape retention although it is also possible that the malleable element could be made of a non-metallic material. The portion of the shaft having the malleable element disposed therein may be manually moved to a direction in which it extends at an angle to another portion of the shaft. As illustrated in FIG. 43, the portion of the shaft adjacent the distal end 424 is positioned at an acute angle relative to the remaining portion of the shaft. Other portions of the shaft may also be angled with respect to another portion such that the shaft is made up of several segments which are angled with respect to one another. The angle itself, which is generally defined at 426, may be configured into the shape illustrated in FIG. 43 having a sharp angle or, alternatively, it may be configured into the orientation illustrated in FIG. 46, which generally has a smoother or more gradual angle or curve. In addition, although FIGS. 43–46 illustrate at least a portion of the shaft being configured at an acute angle relative to another portion, it is realized that angles above 90 degrees may also be utilized.

FIGS. 47–48 illustrate an alternate malleable element. A shaft 428 of a medical instrument includes a malleable element 430 which extends in a generally spiral orientation along an axis 432 of the shaft. The malleable element is capable of shape retention and may be made of a suitable shape retaining material such as metal, plastic, polymer, or any like elements, such that a portion of the shaft may be angled or bent relative to another portion of the shaft and the malleable element retains the angled configuration of the shaft portion.

In FIGS. 47–48, the shaft is manually moved from the configuration shown in FIG. 47 where a shaft axis 432 is generally oriented in a straight line to the shaft orientation illustrated in FIG. 48, whereby the shaft axis 432 is shown having a right angle configuration. Within the shaft, the malleable element may have a variety of orientations. FIGS. 47 and 48 illustrate the malleable element having a generally spiral orientation along the axis of the shaft whereby the malleable element encircles the fluid flow paths 434. It is contemplated that other orientations may also be used where at least a portion of the malleable element extends at an angle relative to the axis of the shaft and where the malleable element is not necessarily oriented in a spiral orientation. By way of example but not limitation the malleable element may also be disposed within the shaft in a fluted or corrugated orientation in addition to numerous other orientations.

FIGS. 49–52 illustrate a further medical instrument generally indicated at 440, likewise having a handle portion generally indicated at 102, a distal end effector generally indicated at 104, and a shaft assembly generally indicated at 106. The shaft assembly is comprised of an elongated shaft 442 having a fluted, corrugated or undulating shape as it extends between a proximal end 444 and a distal end 446. A fluid flow path extends along the elongated shaft and is indicated at 448.

As best shown in FIGS. 50–52, the shaft 442 is comprised of smaller and larger diameter portions 450 and 452, respectively, which define the undulating shape of the outer shaft. The shaft is preferably made of a flexible shape retaining polymer material. At least a portion of the shaft is manually moveable or shapeable so that it can be moved to the position illustrated in FIG. 52 and retain that position. FIG. 49 illustrates the shaft 442 having several portions of the shaft angled relative to other portions of the shaft. These angled portions are shown by way of example but not limitation because it is contemplated that numerous other shapes and configurations are also possible. In the angled configuration illustrated in FIG. 52, a portion of the shaft is curved 90 degree relative to the other portion of the shaft which is shown. The angled configuration also effects the exterior surface of the shaft. In FIG. 52 the shaft surface at the exterior side of the angle—the right side of the shaft illustrated in FIG. 52—the undulations are shown more widely spaced apart. Conversely, the shaft surface at the interior side of the curve—the left side of the shaft illustrated in FIG. 52—has undulations which are more narrowly positioned relative to one another due to the angled orientation of the shaft. While it is preferred that the shaft be made of a material which allows for shape retention, it is also possible that the shaft could flexible in such a way that it allows for the shaft to freely conform to the path defined by its surroundings so as to define a flexible and resilient shaft or, alternately, the shaft may be resilient so that it tends to return to a preformed shape.

The shaft may further comprise a structure analogous to the overlapping spiral shell of BX electrical cable, which allows the shaft to flex relatively freely while protecting the inner conduit. In BX electrical cable, the outer armor shell is cross-sectionally S-shaped, with adjoining spiral sections interlocking, as illustrated in FIG. 51a, while allowing relative shifting to accommodate bending.

FIGS. 53 and 54 illustrate an instrument 460 which is similar to the instrument 440 illustrated in FIGS. 49–52, except that the instrument 460 in FIGS. 53 and 54 includes an outer flexible shaft, generally indicated at 462, which is comprised of a metallic material similar to the shaft in FIGS. 49–52. The shaft 462 in FIGS. 53 and 54 is comprised of smaller and larger diameter portions 464 and 466, respectively. Shaft 462 may be manually moved to an angled position which is illustrated in FIG. 53 in solid lines relative to the straight orientation illustrated in dotted lines. Other orientations are also possible.

FIGS. 55–57 illustrate an alternate instrument 470 having a similar handle portion 102, a distal end effector 104, and a shaft assembly 106 where the shaft assembly is comprised of an outer elongated flexible malleable shaft 472, which generally defines a longitudinal axis 474. There may be one or more fluid flow paths 476.

FIGS. 55 and 56 illustrate, respectively, a straight configuration and an angled configuration. In FIG. 56 at least a portion of the shaft 472 in proximity to the distal end of the shaft is bent, at a location generally indicated at 478, at an angle with respect to another and more proximal portion of the shaft. The angle which is defined relative to the remaining portion of the shaft is an acute angle although other angles are also possible. The shaft 472 is preferably made of a metallic material which has shape retention characteristics so that the distal portion of the shaft is retained in the bent configuration in FIG. 56. Alternatively, it is possible that the shaft may be resilient or freely conforming to the shape of the pathway defined by its surroundings.

FIGS. 58–60 generally illustrate instruments having a shaft comprised of a material which is capable of being preformed into a desired orientation. The shaft may be manufactured from, for example, a thermoformable plastic or polymer which is capable of being heat-formed into a desired orientation example, as well as other plastic and/or metallic materials which may be formed into a desired shape or configuration.

In FIG. 58, an instrument 480 includes a shaft 482, which is comprised of a heat-formable polymer. The polymeric material is heated to a suitable temperature which allows for the shaft to be formed into a desired shape having one or more portions of the shaft being moved to a direction at an angle relative to other portions of the shaft at one or more locations, which in FIG. 58 are represented as lateral or horizontal bends, generally indicated at 486 and 488. The shaft is allowed to cool in the desired shape and may be held within an appropriately shaped cavity or mold during the cooling process so that the shaft retains its angled configuration. While the shaft may retain flexibility characteristics, it is generally resilient in that it is biased to return to its preformed shape. One or more fluid flow paths 484 extend within the shaft and are flexible so as to follow the preformed shape of the outer shaft as illustrated in FIG. 59.

In FIG. 60, instrument 490 similarly includes an elongated shaft 492 which defines a longitudinal shaft axis and is preformed into an angled configuration. The preformed configuration of the shaft 492 is substantially straight along the proximal end of the shaft and is curved at the distal portion of the shaft to define an overall L-shaped configuration.

In addition to those shapes shown in FIG. 58 and FIG. 60, numerous other preformed shapes are also possible depending on the medical procedure employed, the method of approach utilized and the area of the patient's body which requires treatment. By way of example but not limitation, at least one portion of the shaft may have a preformed configuration which is angled in any direction or degree and the shaft may have several angled portions along its length.

Although the instruments in FIGS. 58–60 are shown having a preformed shape, these instruments may also provide a shaft which has flexibility characteristics. For example, at least a portion of the shaft may be resilient so as to allow the shaft to be manually moved or shaped relative to another portion of the shaft upon applying a force and thereafter, once the force is removed, the portion of the shaft will return to its preformed configuration. The flexibility of the shaft also may provide that a portion of the shaft may be moved to increase or decrease the existing angle of the curvatures along the length of the shaft. The longitudinal axis of the shaft may be oriented in a straight orientation during insertion of the instrument through a trocar or other insertion device so as to facilitate insertion. In addition, the shaft assembly in either instrument illustrated in FIGS. 58–60 may include a malleable element as previously described so as to allow further manual movement of at least a portion of the shaft relative to other portions of the shaft so that the shaped portion retains its new shape.

FIGS. 61–65 illustrate an instrument 500 which is similarly comprised of a handle portion 102, a distal end effector assembly 104 and shaft assembly 106. The shaft assembly includes an elongated outer flexible shaft, generally indicated at 502, which extends between a proximal end 504 and a distal end 506. Fluid flow paths 508 extend along the shaft. Shaft shape control rods 510 extend along the shaft between the proximal and distal ends 504 and 506 and are in operative engagement with a control member 512 such as the control knobs illustrated in FIG. 61. Although FIGS. 61–65 illustrate two control rods 510 extending along the length of the shaft, any number of control rods may be used extending to various longitudinal locations of the shaft. The control rods, although shown in FIGS. 61–65 as positioned on the left and right sides of the shaft, may be positioned in other orientations without departing from this aspect of the present invention.

The control rods 510 allow for manipulation of the shaft configuration from the handle portion 102 of the instrument. Movement of the knobs 512 at the handle portion effectuates movement of the shaft along at least a portion of the shaft. Tension, rotation or compression and/or any combination of these forces may be applied to the control rods by the control member. For example, in FIGS. 64 and 65 the shaft is moved from the orientation illustrated in FIG. 64 to that shown in FIG. 65 by tension applied to the proximal portion of the lower control rod 510 illustrated in FIG. 64. Alternatively, the bent configuration in FIG. 65 may be achieved by compressive force being applied to the proximal end portion of the upper control 510 in FIG. 64. A combination of one or more forces applied to one or more of the control members will allow curvature of the shaft in essentially unlimited degrees and direction relative to another portion of the shaft and/or the handle portion.

End Effector Configuration

FIGS. 68–79 illustrate a variety of end effector configurations. These configurations are shown by way of example and not limitation as it will be realized that numerous other orientations may be utilized without departing from this aspect of the present invention. The end effector may be curved in one or more directions and up to 360 degrees. By way of example but not limitation the end effector may have a complex curve, which is a curve which includes two or more simultaneous directions of curvature relative to a straightened end effector configuration. In fact, any number of different end effector orientations are contemplated without departing from the present invention.

Figure 68:
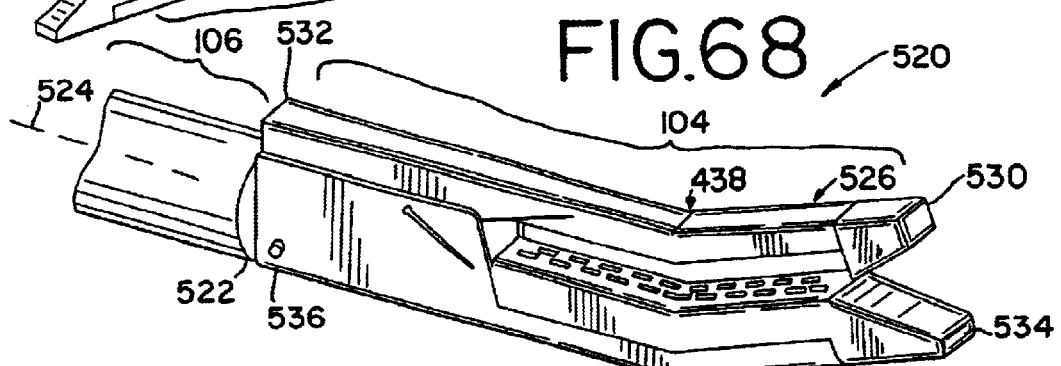
FIG. 68 is a perspective view of the distal portion of an instrument employing an end effector having a portion which is angled in vertical direction relative to the remaining portion of the end effector.
Figure 69:
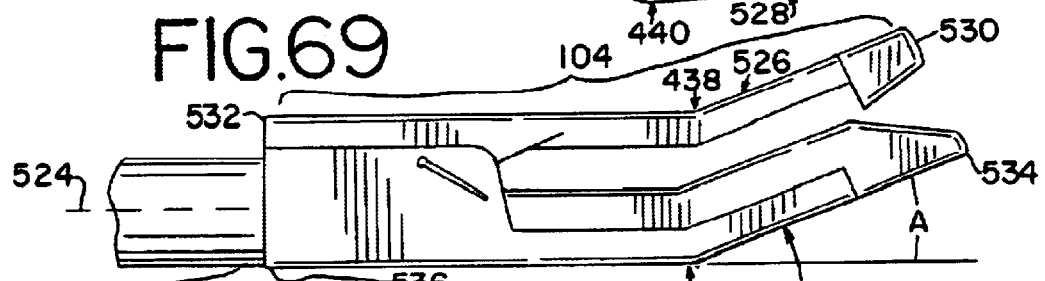
FIG. 69 is a side elevational view of FIG. 68.
Figure 70:
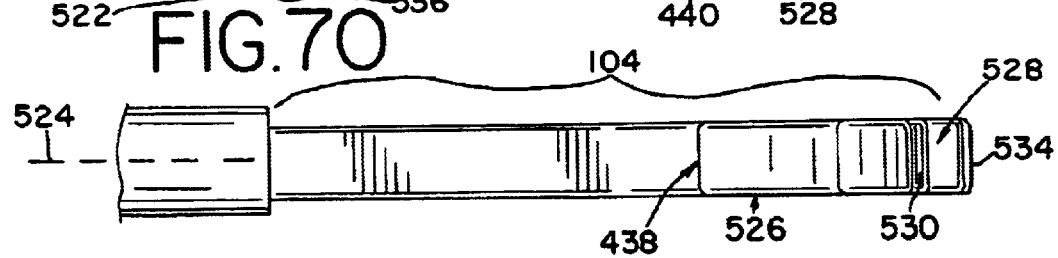
FIG. 70 is a top view of the end effector of FIG. 68.

In FIGS. 68–70 an instrument 520 has an elongated end effector assembly 104 disposed at a distal end 522 of a shaft assembly 106. The shaft generally defines a longitudinal shaft axis 524 at the distal end of the shaft. The end effector includes an upper jaw 526 and a lower jaw 528, which include elements corresponding to those previously described for actuation of the hydraulic medical instrument for closure of the jaws and ejection of the staples. The upper jaw includes a distal end portion 530 and a proximal end portion 532. Likewise, the lower jaw 528 includes a distal end portion 534 and a proximal end portion 536. As best seen in FIGS. 68 and 69, the portion of each upper and lower jaws 526 and 528 adjacent the distal end portions 530 and 534 extends at an angle relative to a more proximal portion of each upper and lower jaw. At locations, generally indicated at 438 and 440, respectively, each angled portion of the upper and lower jaws defines an acute angle A relative to the remaining portion of each of the jaws. The shape or configuration of the end effector in FIGS. 68–70 is shown as having a ramped or angled configuration in a vertical direction relative to another portion of the end effector.

It is contemplated, however, that other angles may be utilized depending on the desired configuration for the medical procedure. The end effector may be angled relative to other directions and degrees so that virtually unlimited configurations are possible for at least a portion of the end effector relative to another portion of the end effector and/or the shaft assembly.

The configuration illustrated in FIGS. 68–70 may be fixed or flexible in a similar manner as previously described relative to the configuration of the shaft. For example, the end effector may be comprised of a material which is predisposed, resilient or biased to the configuration illustrated in FIGS. 68–70, yet is also allowed to flex or bend from such configuration upon manually moving at least a portion of the end effector. The upper and lower jaws may be comprised in whole or in part of a suitable material which is allowed to bend so as to either increase or decrease the angled portion of the end effector. In addition or as an alternative, either or both of the jaws may be comprised of a shape retaining malleable material or element which allows for at least a portion of the end effector to be manually moved relative to another portion.

Figure 71:
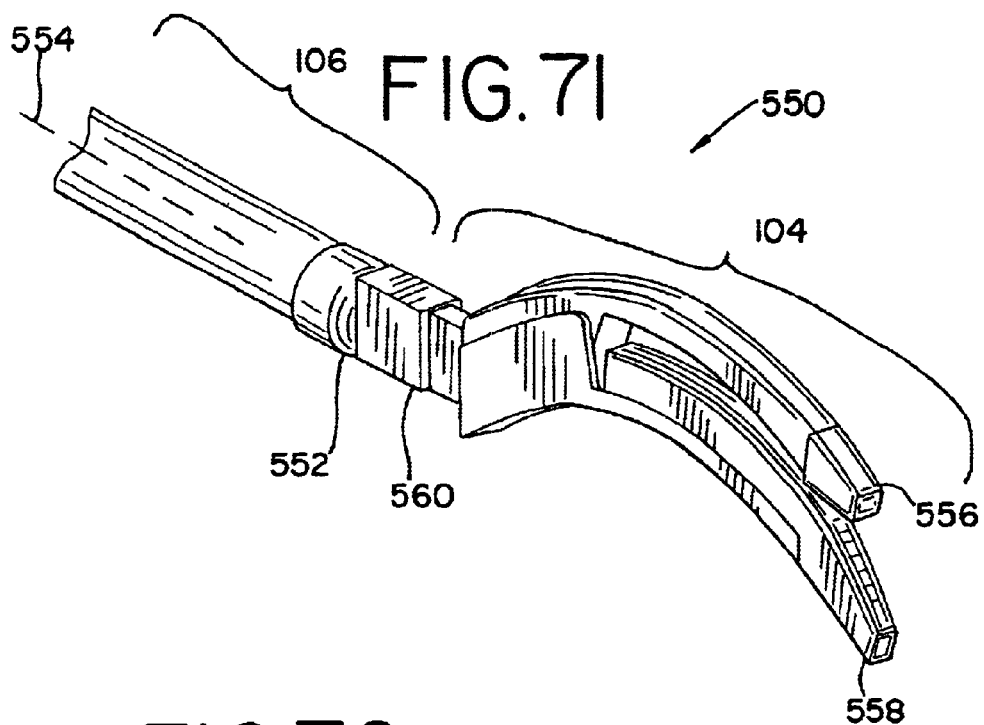
FIG. 71 is a perspective view of the distal portion of an instrument employing an end effector having a curved shape along a vertical direction relative to a longitudinal shaft axis such that one portion of the end effector extends at an angle relative to another portion.
Figure 72:
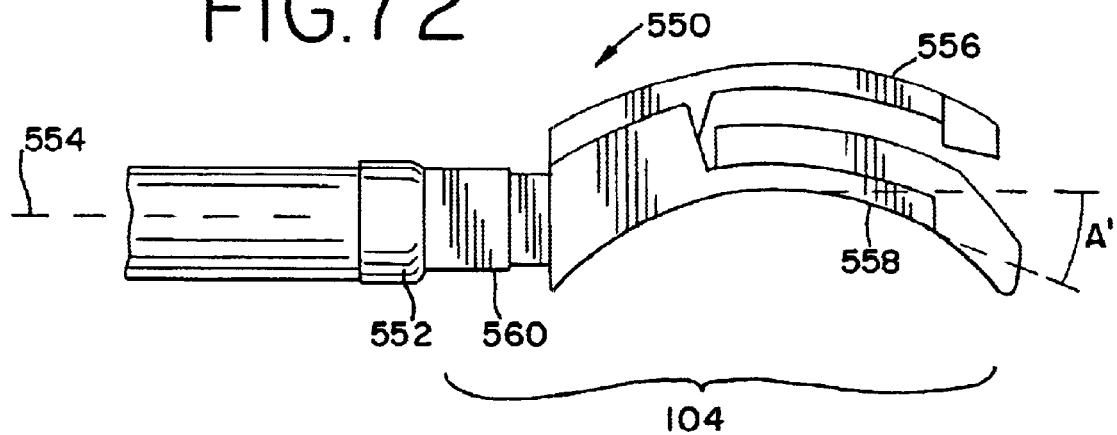
FIG. 72 is a side elevational view of FIG. 71.
Figure 73:
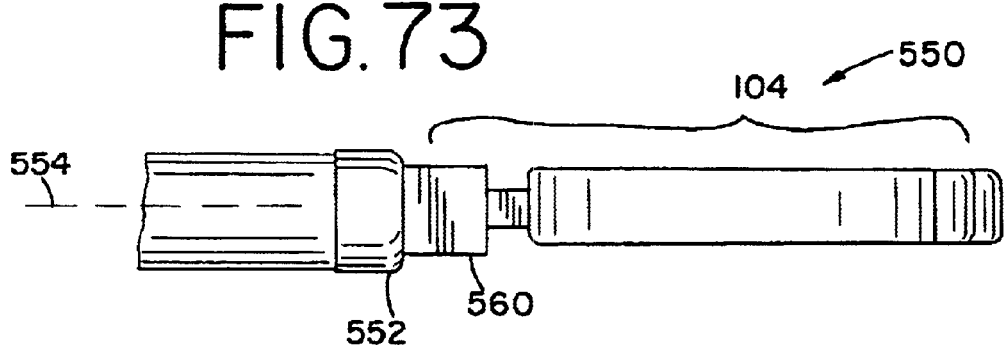
FIG. 73 is a top view of the end effector of FIG. 71.

FIGS. 71–73 illustrate an alternate end effector configuration of an instrument, indicated generally at 550. The elongated end effector assembly 104 is carried at the distal end 552 of the shaft assembly 106. The distal end of the shaft assembly generally defines a longitudinal axis 554. The end effector assembly 104 generally includes upper and lower jaws 556 and 558, respectively, having internal components as previously described herein. Each of the upper and lower jaws are connected to the distal end of the shaft at a common connection 560.

As particularly illustrated in FIG. 72, the upper and lower jaws 556 and 558 are curved along a vertical direction relative to the shaft axis 554, but, as shown in FIG. 73, the jaws are not curved, or are generally straight, along a horizontal direction relative to the shaft axis. As shown by way of example, in FIG. 72, at least one portion of the lower jaw is angled at angle A' relative to another portion of the lower jaw. The upper jaw follows a similar shape. The overall shape of the jaws is an arcuate or curved orientation as best seen FIG. 72. The orientation of the end effector in FIGS. 71–73 is such that the upper jaw provides a convex surface and the lower surface provides a concave surface. It is also possible that the curvature of the end effector may be made up of a plurality of straight segments. Other configurations are also possible including other curvatures.

As compared to FIGS. 68–70, the end effector configuration in FIGS. 71–73 provides a smoother curve and is curved along a majority of the length of the elongated end effector. So, it is contemplated that all or any portion of the end effector may be curved or angled and the degree of curvature may be varied along the length thereof.

FIGS. 74–76 illustrate a further end effector configuration for a medical instrument, generally indicated at 570. The elongated end effector 104 is connected to a shaft assembly 106 at a distal end 572 of the shaft and the shaft generally defines an axis 574 at the distal end thereof. The end effector assembly 104 generally includes upper and lower jaws 576 and 578. As compared to the end effector configurations illustrated in FIGS. 68–73, the end effector of FIGS. 74–76 has a curved configuration in a horizontal direction relative to the longitudinal axis 574 of the shaft, as best shown in FIG. 75. Portions of both the upper and lower jaws 576 and 578 define a concave inner side surface 580 along the inner portion of the curve. A convex surface 582 is defined at the outer side surface of the curve. Along the vertical direction as shown in FIG. 76, the end effector is generally aligned or parallel with the longitudinal axis 574.

FIGS. 78–79 illustrate a yet further medical instrument 590, which essentially combines the features of the end effectors illustrated in FIGS. 71–76 in that the end effector configuration in FIGS. 77–79 is curved in both the horizontal and vertical directions relative to the shaft axis. In this way, FIGS. 78–79 illustrates one type of a complex curve which is curved in two or more directions simultaneously. It is contemplated that numerous other types of complex curves are possible within the scope of the present invention.

In FIGS. 78–79 the end effector assembly 104 is carried at a distal end 592 of the shaft and the shaft generally defines a longitudinal axis at the distal end thereof, indicated at 594. The end effector assembly includes an upper jaw 596 and a lower jaw 598. FIG. 78 best illustrates the curvature of the upper and lower jaws relative to a horizontal direction. A portion of both the upper and lower jaws define an inner concave side surface 600 and, likewise, define an outer convex side surface 602 opposite the concave surface. As best seen in FIG. 79, the end effector assembly 104 is also curved relative to the longitudinal shaft axis 594 in a vertical direction whereby the upper and lower jaws 596 and 598 are curved upwardly and define an upper concave surface 604 and a lower convex surface 606.

As previously mentioned, it is contemplated that a variety of other orientations are possible. For example, the end effector assembly may be curved along its length or a portion thereof to the right or to the left, upwards or downwards, or any combination thereof. Although the angle of curvature is shown as generally being an acute angle, other angles are also possible. In addition, the degree and sharpness of the curvature may vary. In addition, either or both of the upper and lower jaws may be comprised of a rigid material or, alternatively, may be flexible so as to allow manual movement of at least a portion of the end effector assembly relative to another portion.

Figure 66:
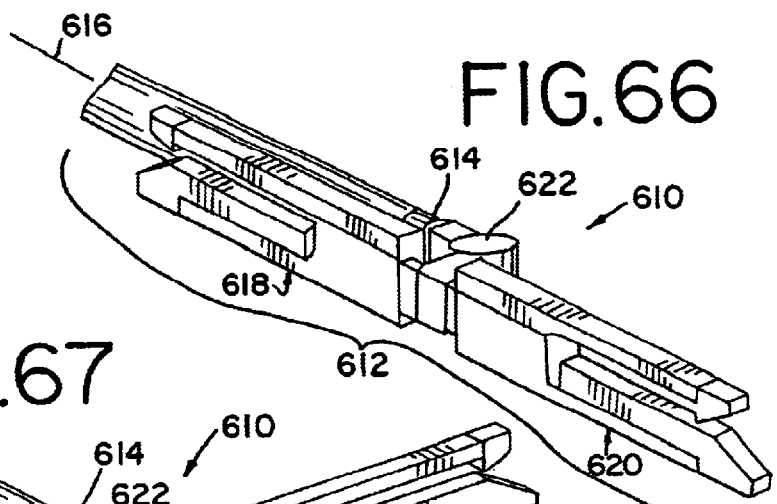
FIG. 66 illustrates a perspective view of the distal portion of an instrument employing a dual-headed end effector.
Figure 67:
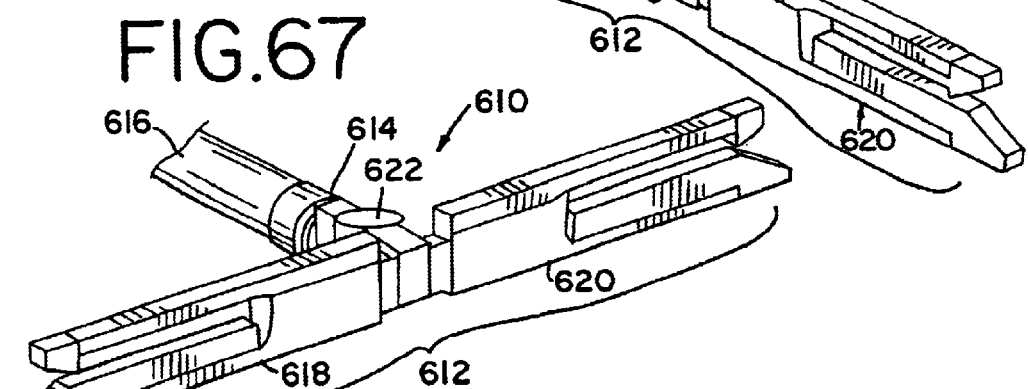
FIG. 67 illustrates the end effector of FIG. 66 rotated 90 degrees.

Turning to FIGS. 66 and 67, another aspect of the present invention may utilize a dual-headed end effector assembly, generally indicated at 612. The end effector assembly 612 is connected to a distal end 614 of the shaft, and the shaft generally defines a longitudinal shaft axis 616. The end effector assembly 612 includes first and second end effectors 618 and 620, which are connected to each other at their proximal ends in end-to-end alignment. Both proximal ends are further connected to a common hub or articulation joint 622, which is connected to the distal end 614 of the shaft. The hub 622 is rotatable relative to the shaft so as to allow lateral movement of the end effector assembly 612 relative to the longitudinal shaft axis.

FIG. 66 illustrates the first and second end effectors disposed in a generally aligned parallel relationship relative to the longitudinal shaft axis 616. FIG. 67 illustrates the first and second end effectors after rotation of the hub 622 approximately 90 degrees relative to the position shown in FIG. 66. The configuration illustrated in FIG. 67 shows an overall T-shaped dual-headed end effector. The hub may be spring loaded so that it normally is disposed in the position illustrated in FIG. 67. During initial insertion of the medical instrument 610 into the patient's body, a trocar or other insertion device may be used to bias the instrument to the position illustrated in FIG. 66. Thereafter, once the distal end of the trailing end effector clears the trocar, the end effector assembly will assume the position in FIG. 67. Although the end effector assembly is shown in FIG. 67 at a ninety degree angle relative to FIG. 66, other angular positions are also possible and may depend upon the medical procedures, medical approaches and internal body areas to be contacted.

As can be seen from the above description, the present invention has several different aspects and features, which are not limited to the specific device shown in the attached drawings or to the specific procedures discussed. Various of these features may be embodied in other devices for carrying out other procedures, including but not limited to stapling, cutting, grasping, coagulating or other surgical procedures.

Although shown in a manual form, for direct control by the surgeon, the present invention is also applicable in robotically controlled procedures. The hydraulic actuation of the present invention particularly lends itself to small diameter instruments, multi-axis articulation and large force (e.g., clamping or cutting force) generation, which are not only advantageous in manual applications but are also particularly useful in robotic applications, where the instrument operation is remotely controlled through a robotic controller module or unit.

In a robotic application, for example, the end effector assembly could be attached, by way of an elongated shaft, with a remote hydraulic pressure source. The hydraulic pressure source (which may include multiple independent hydraulic pressure sources) could be remotely controlled via electronic or electro-mechanical controller operated by programmable microprocessor alone or in combination with manual control or voice control commands or both, as already known in the art of remote robotic control.

The invention claimed is:

1. A hydraulically actuated endoscopic medical instrument, comprising:
    an elongated shaft including a proximal end and a distal end and generally defining a longitudinal shaft axis at the distal end thereof;
    an elongated end effector at the distal end of the elongated shaft, at least a portion of the end effector extending at an angle to another portion of the end effector;
    a handle portion at the proximal end of the elongated shaft, the handle portion including a plurality of hydraulic pressure sources, a first manually movable member movable to actuate one pressure source, a second manually movable member movable to actuate another pressure source, a first locking member for releasably locking the first movable member in the actuated position and a second locking member for releasably locking the second movable member in the actuated position; and
    a fluid flow path extending between the handle portion and the end effector through the elongated shaft.

2. The medical instrument of claim 1 wherein the end effector is curved.

3. The medical instrument of claim 1 wherein the one portion of the end effector extends at an acute angle relative to another portion of the end effector.

4. A hydraulically actuated endoscopic medical instrument, comprising:
    an elongated flexible shaft including a proximal end and a distal end, at least a portion of the shaft being manually movable to a direction in which it extends at an angle to another portion of the shaft;
    an end effector at the distal end of the elongated shaft;
    a handle portion at the proximal end of the elongated shaft, the handle portion including a plurality of hydraulic pressure sources, a first manually movable member movable to actuate one pressure source, a second manually movable member to actuate another pressure source, a first locking member for releasably locking the first movable member in the actuated position and a second locking member for releasably locking the second movable member in the actuated position; and
    a fluid flow path extending between the handle portion and the end effector through the elongated shaft.

5. The medical instrument of claim 4 wherein at least a portion of the shaft is made of plastic.

6. The medical instrument of claim 4 wherein at least a portion of the shaft is made of a metallic material.

7. The medical instrument of claim 4 further comprising an elongated malleable element extending along the shaft.

8. The medical instrument of claim 7 wherein the malleable element is made of metal.

9. The medical instrument of claim 7 wherein the malleable element extends from the handle portion to the end effector.

10. The medical instrument of claim 7 wherein shaft defines an axis and the malleable element is generally aligned parallel to the axis of the shaft.

11. The medical instrument of claim 7 wherein the shaft defines an axis and at least a portion of the malleable element extends at an angle relative to the axis of the shaft.

12. The medical instrument of claim 7 further including shaft shape control rods extending from the handle portion to a location along the shaft.

13. The medical instrument of claim 11 wherein the malleable element extends in a generally spiral orientation along the axis of the shaft.

14. A hydraulically actuated endoscopic medical instrument, comprising:
    an elongated flexible shaft including a proximal end and a distal end, at least a portion of the shaft being manually movable to a direction in which it extends at an angle to another portion of the shaft;
    an elongated end effector at the distal end of the elongated shaft, at least a portion of the end effector extending at an angle to another portion of the end effector;
    a handle portion at the proximal end of the elongated shaft, the handle portion including a plurality of hydraulic pressure sources, a first manually movable member movable to actuate one pressure source, a second manually movable member to actuate another pressure source, a first locking member for releasably locking the first movable member in the actuated position and a second locking member for releasably locking the second movable member in the actuated position; and
    a fluid flow path extending between the handle portion and the end effector through the elongated shaft.

* * * * *